(12) United States Patent
Hahn et al.

(10) Patent No.: US 8,895,069 B2
(45) Date of Patent: Nov. 25, 2014

(54) DRUG DELIVERY SYSTEM USING HYALURONIC ACID-PEPTIDE CONJUGATE MICELLE

(75) Inventors: Sei Kwang Hahn, Pohang (KR); Choun-Ki Joo, Seoul (KR); Yoon Keun Kim, Pohang (KR); Seung Kew Yoon, Seoul (KR); Eun Ju Oh, Busan (KR); Ki Su Kim, Suwon (KR); Hyemin Kim, Daegu (KR); Kitae Park, Jeonju (KR); Jeong-A Yang, Cheongju (KR); Jun-Sub Choi, Yongin (KR); You Me Tae, Incheon (KR); Wonhee Hur, Seoul (KR)

(73) Assignee: Postech Academy-Industry Foundation, Pohang (KR)

( * ) Notice: Subject to any disclaimer, the term of this patent is extended or adjusted under 35 U.S.C. 154(b) by 0 days.

(21) Appl. No.: 13/326,477

(22) Filed: Dec. 15, 2011

(65) Prior Publication Data

US 2012/0294945 A1 Nov. 22, 2012

(30) Foreign Application Priority Data

May 16, 2011 (KR) .................. 10-2011-0047497
Nov. 3, 2011 (KR) .................. 10-2011-0114013

(51) Int. Cl.
| | | |
|---|---|---|
| *A61K 31/573* | (2006.01) | |
| *A61K 31/704* | (2006.01) | |
| *A61P 11/06* | (2006.01) | |
| *A61P 9/00* | (2006.01) | |
| *A61K 31/353* | (2006.01) | |
| *A61K 9/107* | (2006.01) | |
| *A61K 47/48* | (2006.01) | |
| *A61K 31/352* | (2006.01) | |

(52) U.S. Cl.
CPC ............ *A61K 9/107* (2013.01); *A61K 47/4823* (2013.01); *A61K 47/48238* (2013.01); *A61K 47/488* (2013.01); *A61K 31/352* (2013.01); *A61K 31/573* (2013.01); *A61K 31/704* (2013.01); *Y10S 977/795* (2013.01); *Y10S 977/906* (2013.01)
USPC ............ 424/489; 514/456; 514/180; 514/34; 427/2.14; 977/795; 977/906

(58) Field of Classification Search
None
See application file for complete search history.

(56) References Cited

U.S. PATENT DOCUMENTS

2005/0123505 A1* 6/2005 Chen et al. ............. 424/78.27

FOREIGN PATENT DOCUMENTS

| | | |
|---|---|---|
| EP | 1857467 | 11/2007 |
| KR | 10-2009-0013696 | 2/2009 |
| KR | 10-2010-0100497 | 9/2010 |
| KR | 10-2010-0133688 | 12/2010 |
| WO | WO 03/105765 | * 12/2003 |

OTHER PUBLICATIONS

Oh et al "Anti-Flt1 peptide—Hyaluronate conjugate for the treatment of retinal neovascularization and diabetic retinopathy" (Jan. 4, 2011) Biomaterials 32: 3115-3123.*
Gasparini et al "Combination of Antiangiogenic Therapy With Other Anticancer Therapies: Results, Challenges, and Open Questions" Journal of Clinical Oncology (Feb. 20, 2005) vol. 23:6, pp. 1295-1311.*
Kwon et al. "Pharmaceutical Evaluation of Genistein-loaded Pluronic Micelles for Oral Delivery" Arch Pharm Res (2007) 30:9, pp. 1138-1143.*
Choi et al "Self-assembled hyaluronic acid nanoparticles for active tumor targeting" (Sep. 26, 2009) Biomaterials 31: 106-114.*
Kwon et al ("Pharmaceutical Evaluation of Genistein-loaded Pluronic Micelles for Oral Delivery" Arch Pharm Res (2007) 30(9): 1138-1143).*
Choi et al (Biomaterials (Sep. 26, 2009) 31: 106-114).*
Wikipedia "Tetrabutylammonium hydroxide" downloaded Mar. 20, 2014 from http://en.wikipedia.org/wiki/Tetrabutylammonium_hydroxide.*
Wikipedia "Hyaluronan" downloaded Mar. 20, 2014 from http://en.wikipedia.org/wiki/Hyaluronan.*
Kwon (Arch Pharm Res (2007) 30(9): 1138-1143).*
Choi (Biomaterials (Sep. 26, 2009) 31 : 106-114).*
Eun Ju Oh et al, Anti-Flt 1 peptide- Hyaluronate conjugate for the treatment of retinal neovascularization and diabetic retinopathy, Biomaterials 32 (2011)3115-3123 Jan. 28, 2011.

* cited by examiner

*Primary Examiner* — Karlheinz R Skowronek
*Assistant Examiner* — Mindy Newman
(74) *Attorney, Agent, or Firm* — Lexyoume IP Meister, PLLC

(57) ABSTRACT

The present invention relates to a drug delivery composition comprising a hyaluronic acid-peptide conjugate micelle and a production method thereof. According to the drug delivery composition and the production method of the drug-loaded, hyaluronic acid-peptide conjugate micelle of the present invention, the reaction for encapsulating can proceed in a mixed solvent of an aqueous solvent and an organic solvent. Therefore, the present invention can be applied to various types of water-insoluble active components and the biocompatible and biodegradable derivative can encapsulate a drug to provide a drug-loaded micelle, which is safe to be applied for human bodies. Moreover, the micelle has a therapeutic effect from the peptide contained therein, which can act in combination with the drug as packing therein. Therefore, the drug delivery composition and its production method can be utilized in the field of producing a sustained release formulation with an extended duration of the medicinal effect.

24 Claims, 29 Drawing Sheets

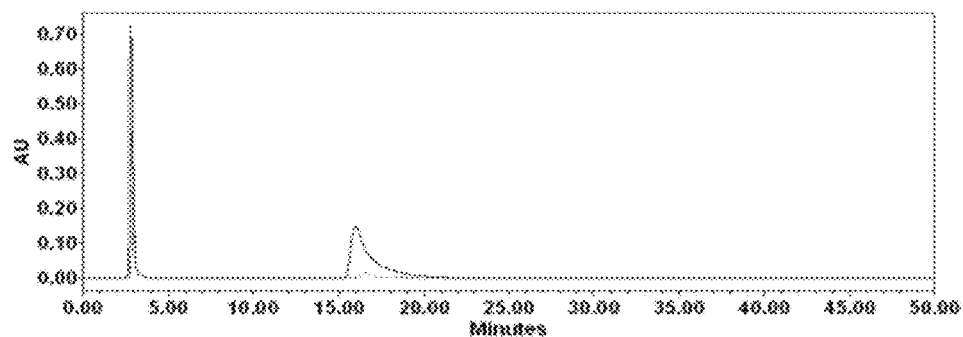
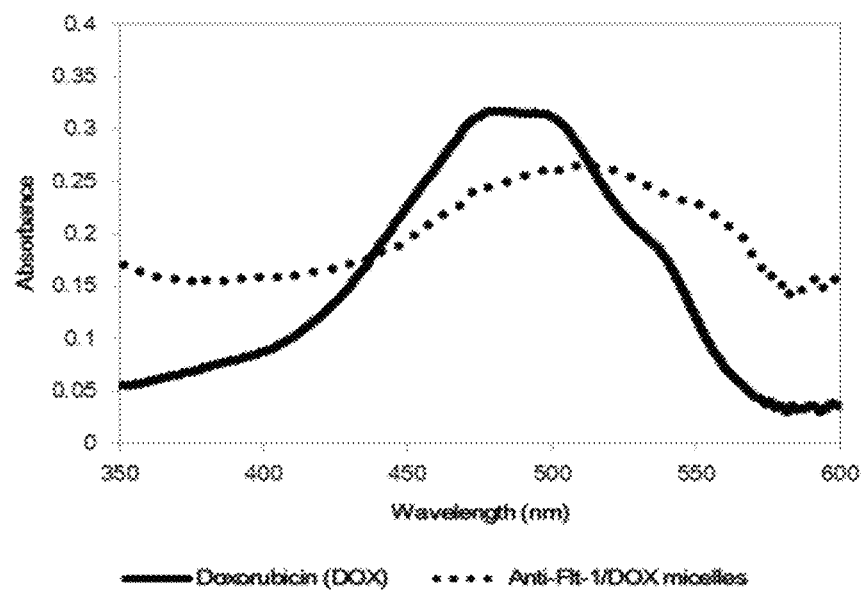

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: anti-Flt1 peptide

<400> SEQUENCE: 1

Gly Asn Gln Trp Phe Ile
 1               5

<210> SEQ ID NO 2
<211> LENGTH: 7
<212> TYPE: PRT
<213> ORGANISM: Artificial Sequence
<220> FEATURE:
<223> OTHER INFORMATION: anti-Flt1 peptide

<400> SEQUENCE: 2

Lys Gly Asn Gln Trp Phe Ile
 1               5

<210> SEQ ID NO 3
<211> LENGTH: 7
<212> TYPE: PRT
<213> ORGANISM: Artificial Sequence
<220> FEATURE:
<223> OTHER INFORMATION: anti-Flt1 peptide

<400> SEQUENCE: 3

Gly Gly Asn Gln Trp Phe Ile
 1               5
```

US 8,895,069 B2

DRUG DELIVERY SYSTEM USING HYALURONIC ACID-PEPTIDE CONJUGATE MICELLE

CROSS REFERENCE TO RELATED APPLICATION

This application claims priority to and the benefit of Korean Patent Application No. 10-2011-0047497 filed on May 19, 2011, and Korean Patent Application No. 10-2011-0114013 filed on Nov. 3, 2011, which are hereby incorporated by reference for all purposes as if fully set forth herein.

BACKGROUND OF THE INVENTION (a) Field of the Invention

The present invention relates to a drug delivery composition comprising a hyaluronic acid-peptide conjugate micelle and a production method thereof. More specifically, the present invention is directed to a method of producing a drug-loaded, hyaluronic acid-peptide conjugate micelle, and a drug-loaded, hyaluronic acid-peptide micelle produced thereby, which can be adopted for a drug delivery system for various water-insoluble drugs, can be applied for a human body since the drug is packing inside a biocompatible and biodegradable micelle delivery system, and can provide an extended duration for a medicinal effect, and wherein the drug can also act in combination with a therapeutic effect of the micelle delivery system itself.

(b) Description of the Related Art

Amphiphilic polymers form a micelle structure in an aqueous solution since the water solubility of their hydrophilic moiety greatly differs from that of their hydrophobic moiety. In the aqueous solution, the micelle has a unique core-shell structure wherein the hydrophobic moieties form an inner core and the hydrophilic moieties form an outer shell. The inner cores of such micelle can be filled with water-insoluble drugs, thereafter which would show a greatly-enhanced water solubility and an extended duration of an medicinal effect. Furthermore, it is possible to control a drug distribution in a body depending on the size of the micelle and to deliver a drug onto a target depending on the surface properties thereof. For that reason, recent studies have been underway to develop micelles as a drug delivery system for the water insoluble drug.

Researches have been conducted to utilize various hydrophilic polymers for the formation of the outer sell, and as a representative example, polyethylene glycol (PEG) has been widely used. Although PEG is one of typical biopolymer materials officially approved by FDA, when being repeatedly injected, the PEG-Liposome conjugate has been reported to suffer accelerated blood clearance (ABC) wherein the administered drug is rapidly lost in a body.

SUMMARY OF THE INVENTION

Thus, the present invention is to provide a drug delivery composition comprising a drug-loaded, hyaluronic acid-peptide conjugate micelle applicable to water-insoluble medicinal ingredients such as a water-insoluble medicine, a method of delivering a drug by using the hyaluronic acid-peptide conjugate micelle, and a method of producing the drug-loaded, hyaluronic acid-peptide conjugate micelle.

It includes the pictures of the corneas from the normal control group, the negative control group (NV control), the positive control group treated with Avastin, the anti-Flt1 peptide (GGNQWFI) (SEQ ID NO: 3) test group, and the hyaluronic acid-peptide conjugate (HA-GGNQWFI) test group, respectively.

Figure 13:
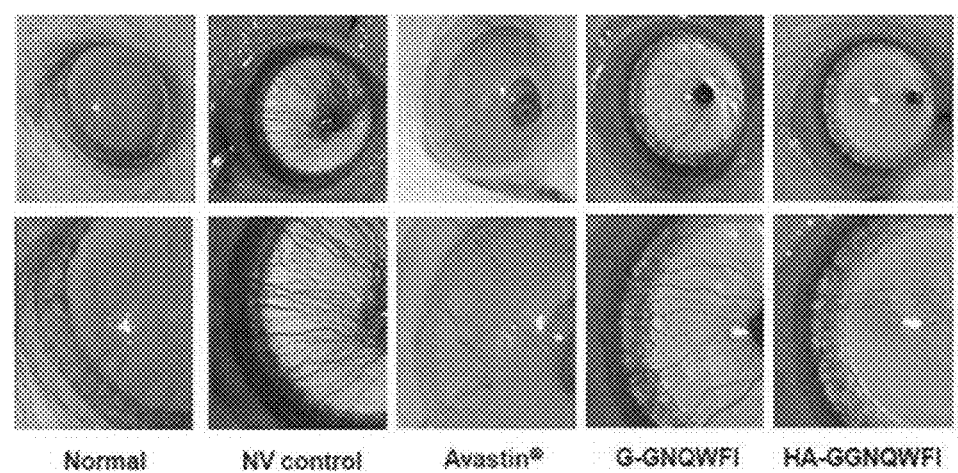
FIG. 13 is a view illustrating an effect of inhibiting corneal neovascularization by the hyaluronic acid-peptide conjugate.
Figure 14:
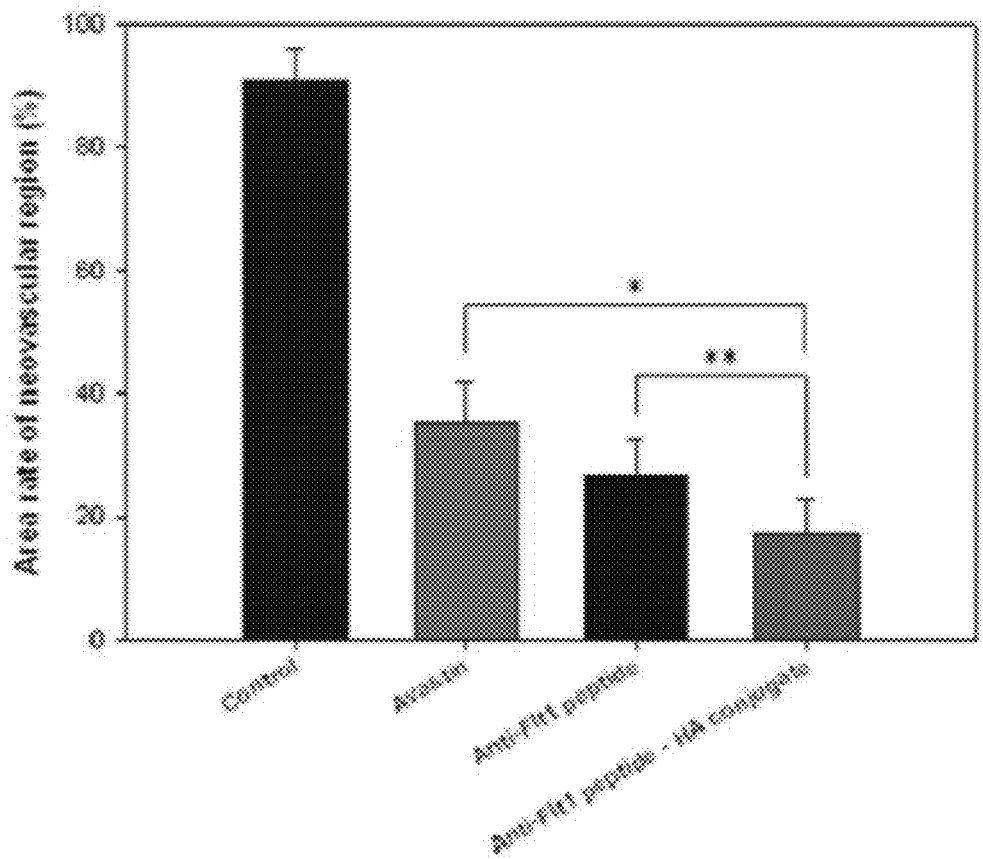

FIG. 14 is a view illustrating the results of quantitatively analyzing the effect of inhibiting corneal angiogenesis as shown in FIG. 13 with using Image J program (* P=0.002 and ** P=0.028).

Figure 15A:
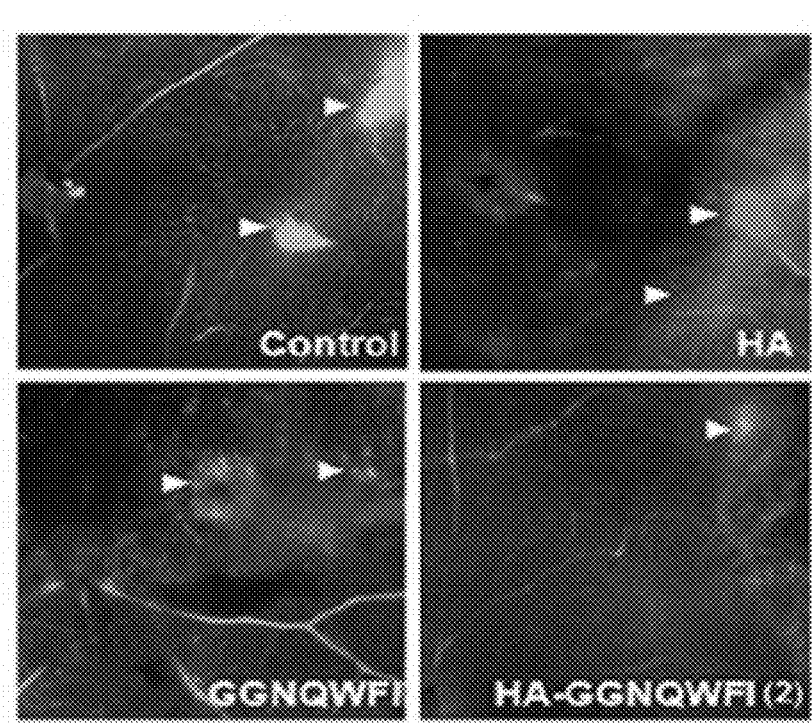
Figure 15B:
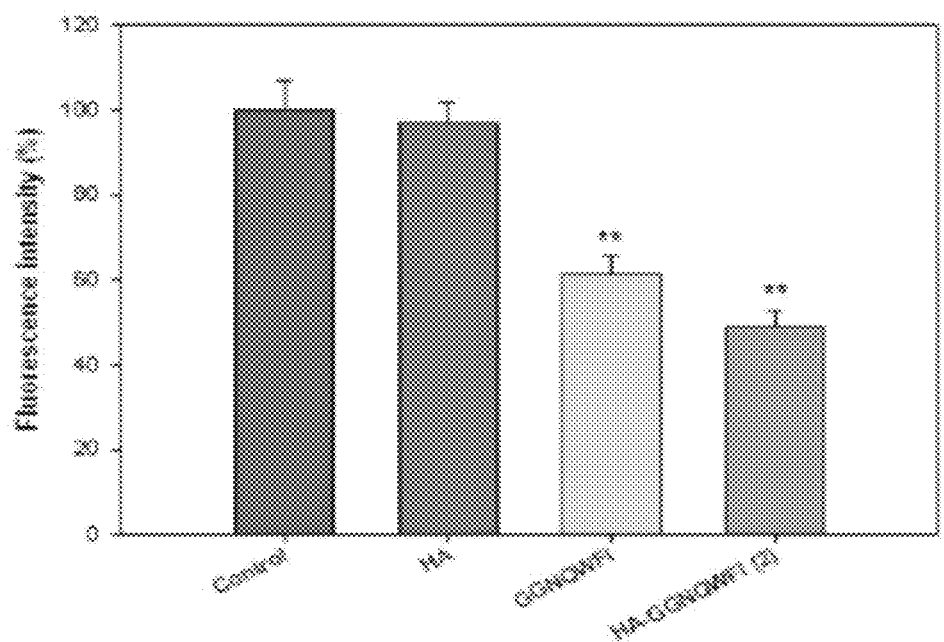

FIG. 15 is a view illustrating the effect of inhibiting retinal and choroidal neovascularization (CNV) by the hyaluronic acid-peptide conjugate. FIG. 15a is fluorescence microscopic images for the treated retinas from the negative control group, the hyaluronic acid test group, the anti-Flt1 peptide (GGNQWFI) (SEQ ID NO: 3) test group, and the hyaluronic acid-peptide conjugate test group, respectively. The original magnification was 100×. FIG. 15b is a view illustrating the results of quantitatively analyzing the fluorescence intensity of CNV lesion with using Image J Program (with respect to the negative control group, ** P<0.01, n=6).

Figure 16A:
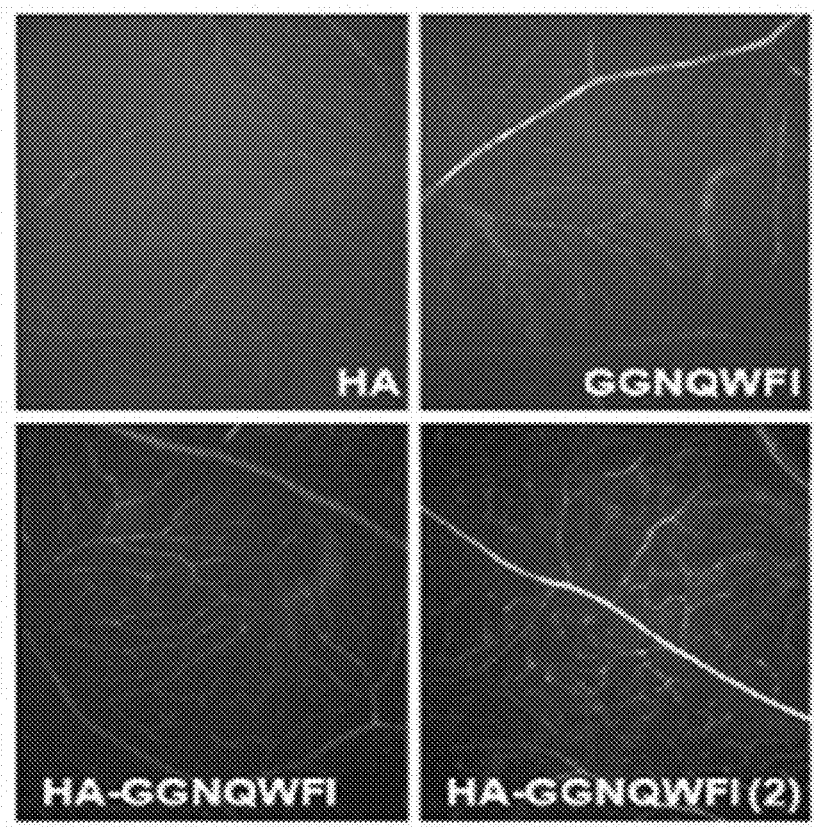
Figure 16B:
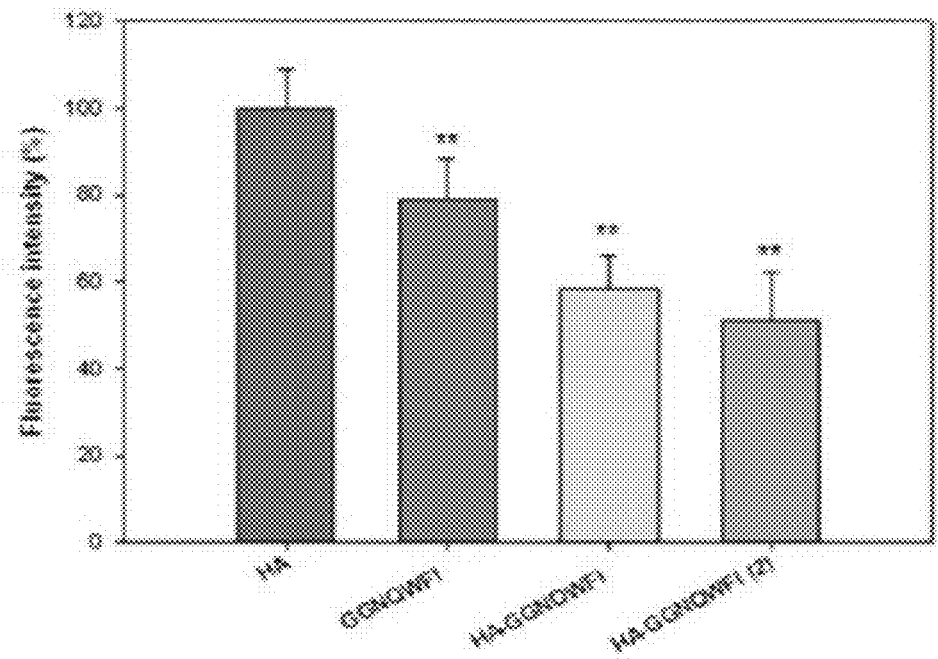

FIG. 16 is a view illustrating the effect of inhibiting vascular hyperpermeability from diabetic retinopathy by the hyaluronic acid-peptide conjugate. FIG. 16a is fluorescence microscopic images for the retinas treated with hyaluronic acid, anti-Flt1 peptide (GGNQWFI) (SEQ ID NO: 3), the hyaluronic acid-peptide conjugate with a lower peptide content (HA-GGNQWFI), and the hyaluronic acid-peptide conjugate with a higher peptide content (HA-GGNQWFI(2)), respectively. The original magnification was 100×. FIG. 16b is a view illustrating the results of quantitatively analyzing the fluorescence intensity of the retina by using Image J Program (with respect to the hyaluronic acid test group, ** P<0.01, n=10).

Figure 17:
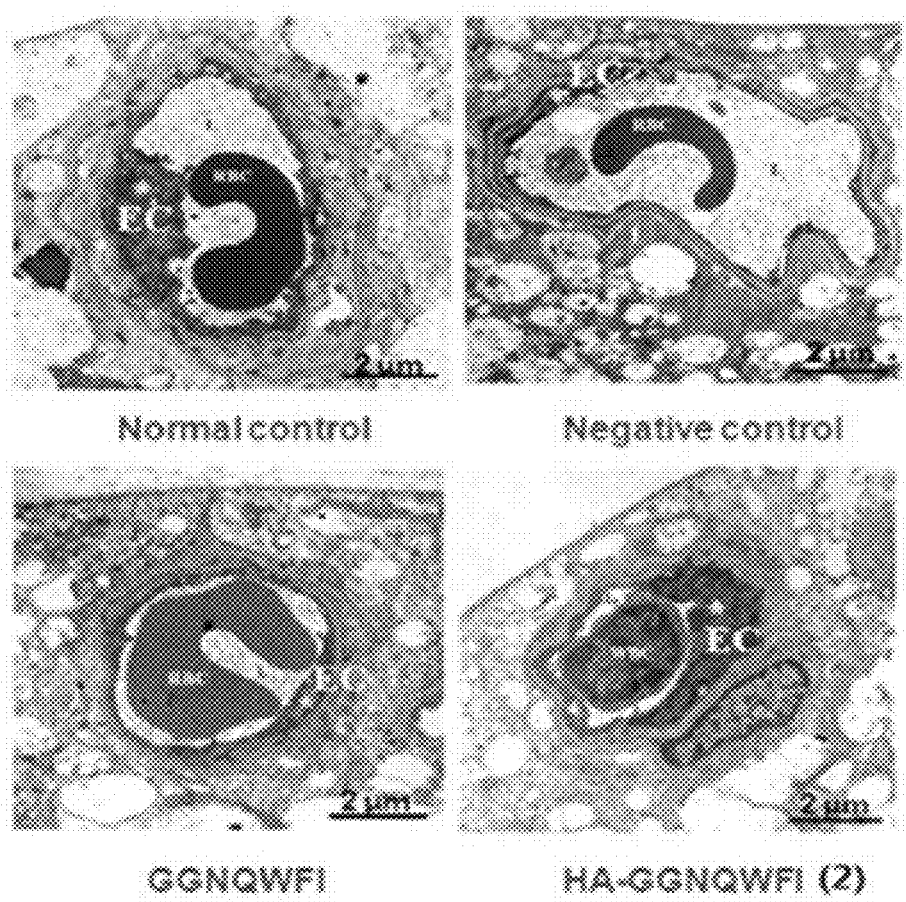

FIG. 17 is electron microscopic images of the retinas from the normal control group, the negative control group, the anti-Flt1 peptide (GGNQWFI) (SEQ ID NO: 3) test group, and the test group of the hyaluronic acid-peptide conjugate with a higher peptide content (HA-GGNQWFI(2)), respectively. (L: lumen of vessel, *: endothelial cell, RBC: red blood cell, WBC: white blood cell) The scale bar is 2 μm.

Figure 18:
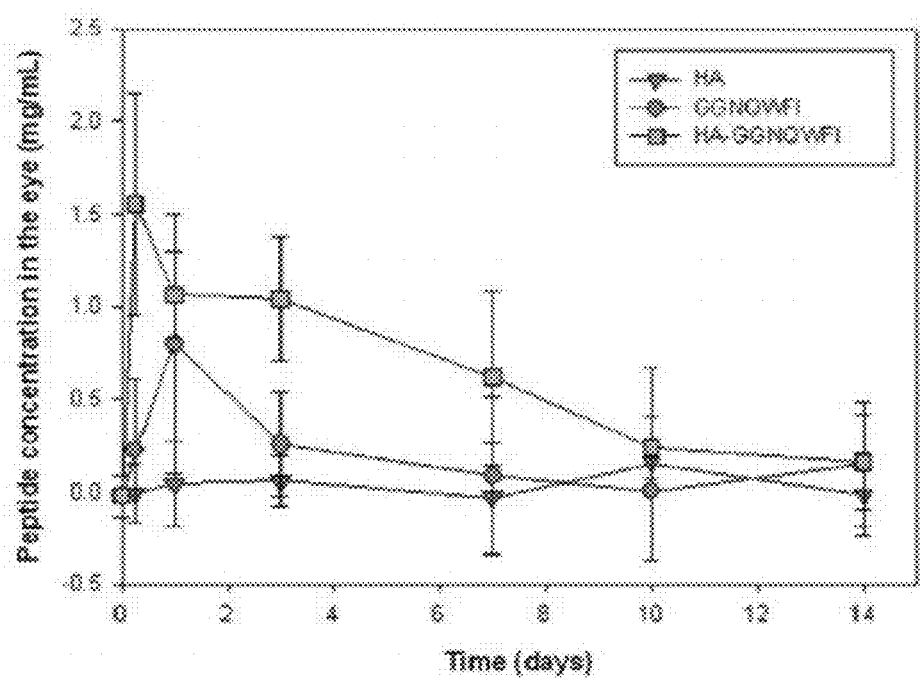

FIG. 18 is a view illustrating the concentrations of anti-Flt1 peptide after the SD rats were injected once with hyaluronic acid, anti-Flt1 peptide (GGNQWFI) (SEQ ID NO: 3), and the hyaluronic acid-peptide conjugate with a lower peptide content (HA-GGNQWFI) into their vitreous bodies (n=6).

Figure 19:
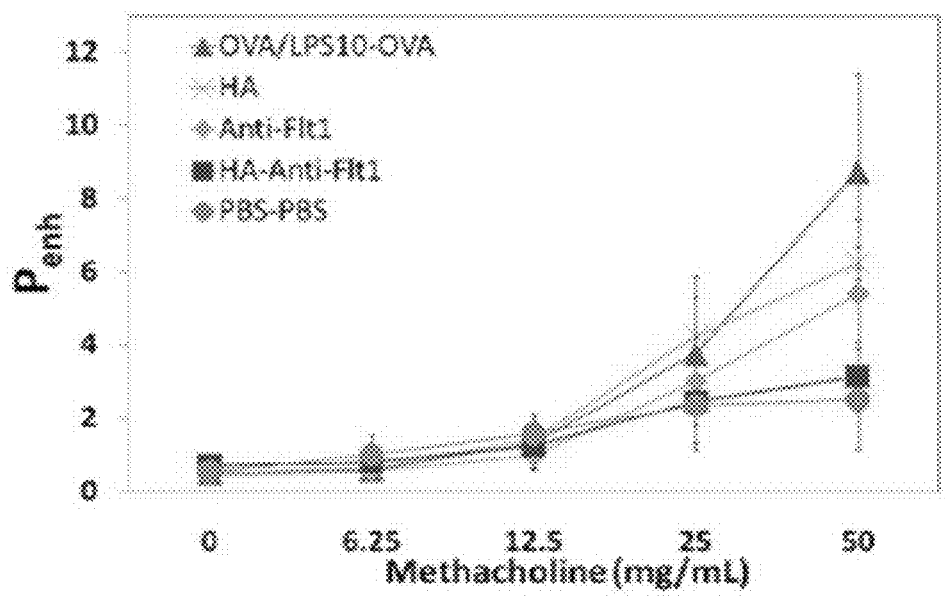

FIG. 19 is a view illustrating methacholine airway hypersensitivity (AHR) for the normal control group, the negative control group, the hyaluronic acid test group, the anti-Flt1 peptide (GGNQWFI) (SEQ ID NO: 3) test group, and the test group of the hyaluronic acid-peptide conjugate of Preparation Example 3.

Figure 20:
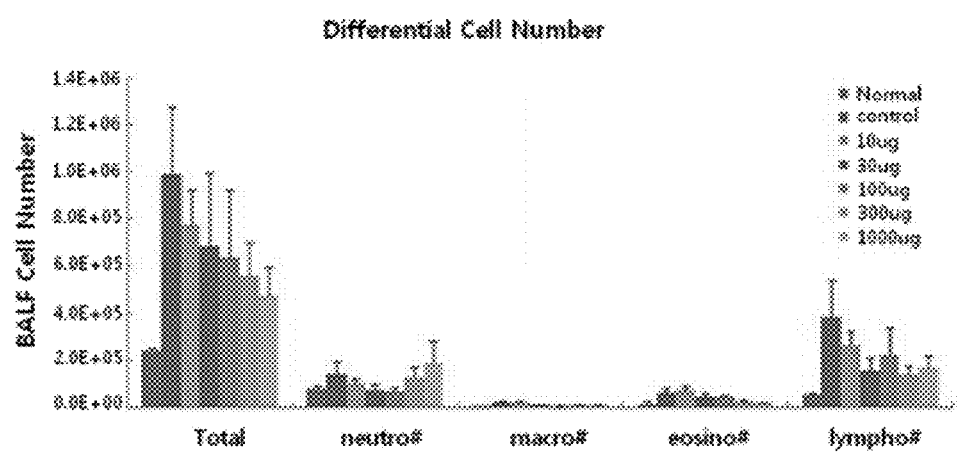

FIG. 20 is a view illustrating bronchoalveolar lavage (BAL) cellularity from the normal control group, the negative control group, and the test group of the hyaluronic acid-peptide conjugate of Preparation Example 3.

Figure 21:
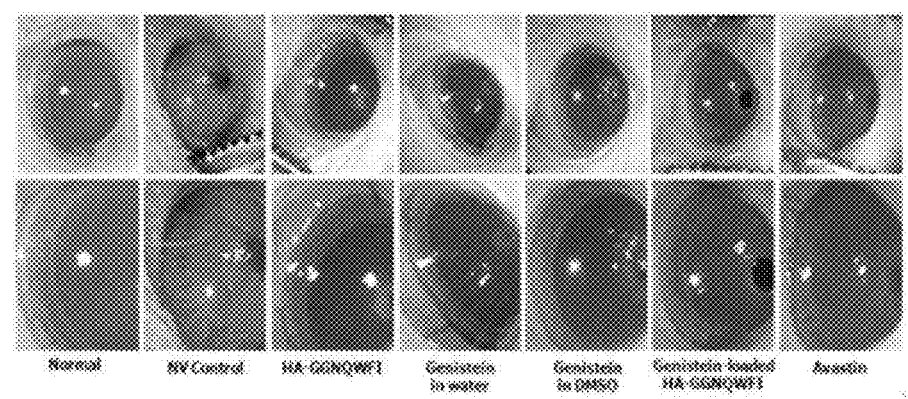

FIG. 21 is a view illustrating the effect of inhibiting corneal angiogenesis by the genistein-loaded, hyaluronic acid-peptide conjugate micelle of Example 1. It comprises the photographs of the corneas of the normal control group, the negative control group, the test groups of the hyaluronic acid-peptide conjugate of Preparation Example 3, genistein, and the genistein-loaded, hyaluronic acid-peptide conjugate micelle of Example 1, and the positive control group treated with Avastin.

Figure 22:
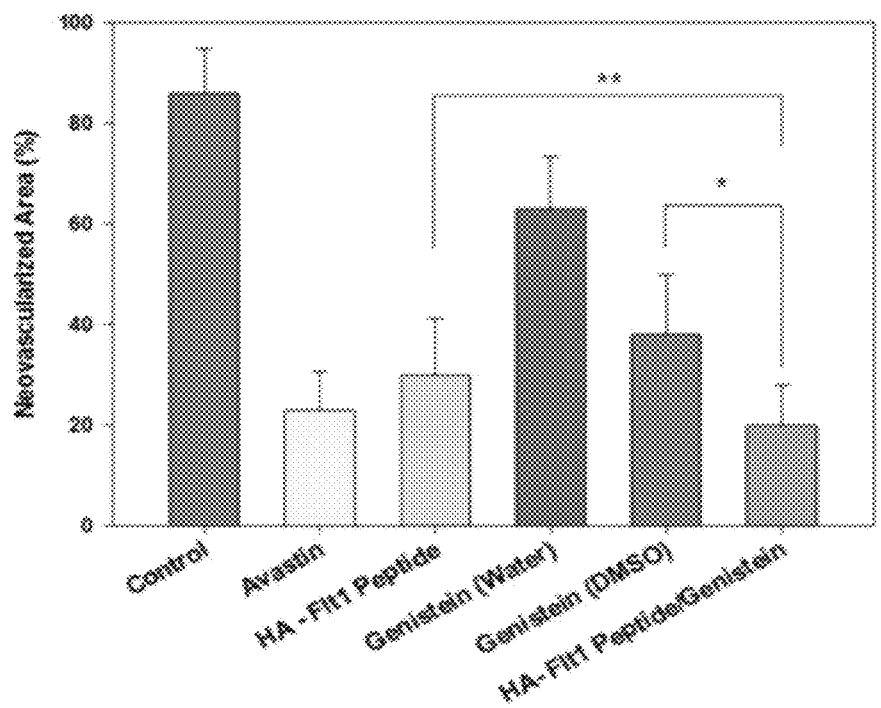

FIG. 22 is a view illustrating the results of quantitative analysis for the effect of inhibiting corneal angiogenesis of FIG. 21 with Image J program.

Figure 23A:
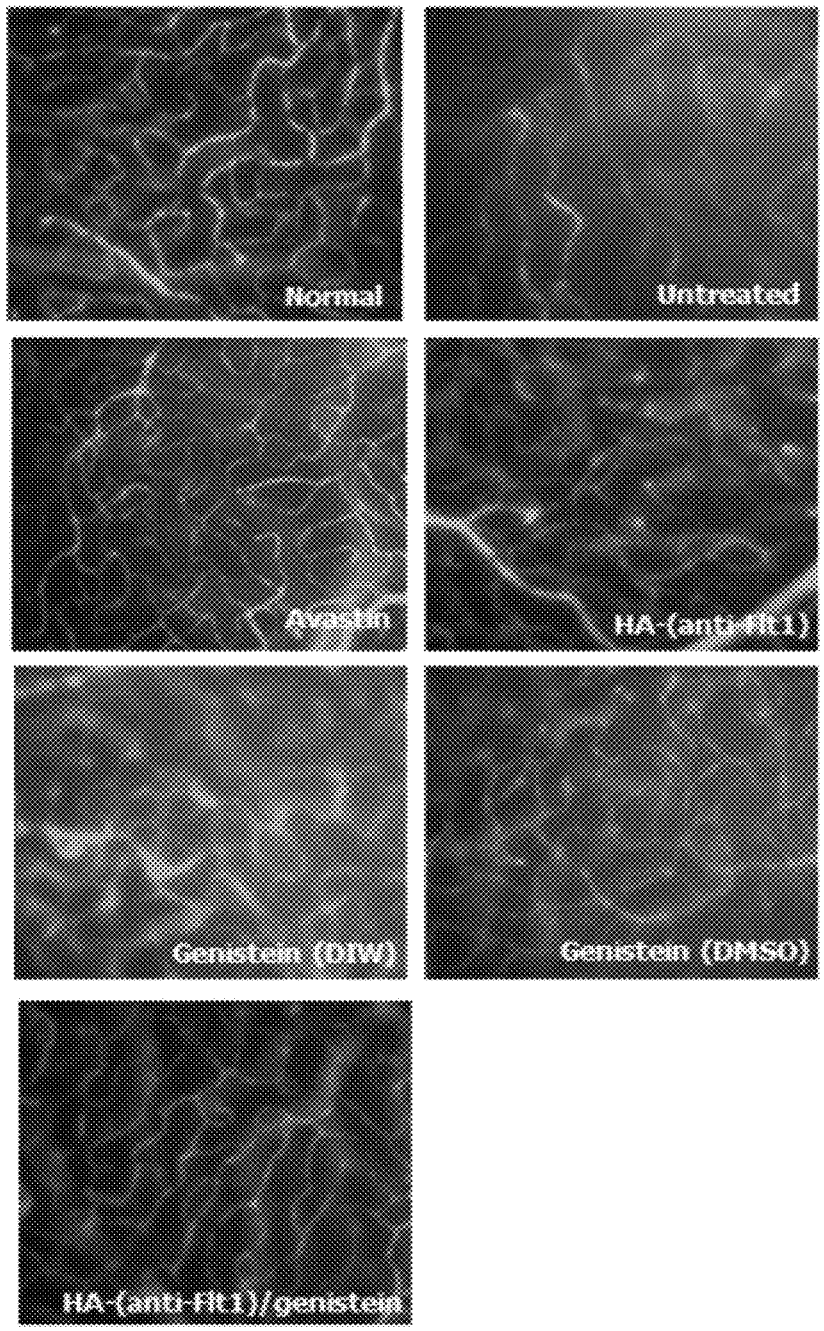
Figure 23B:
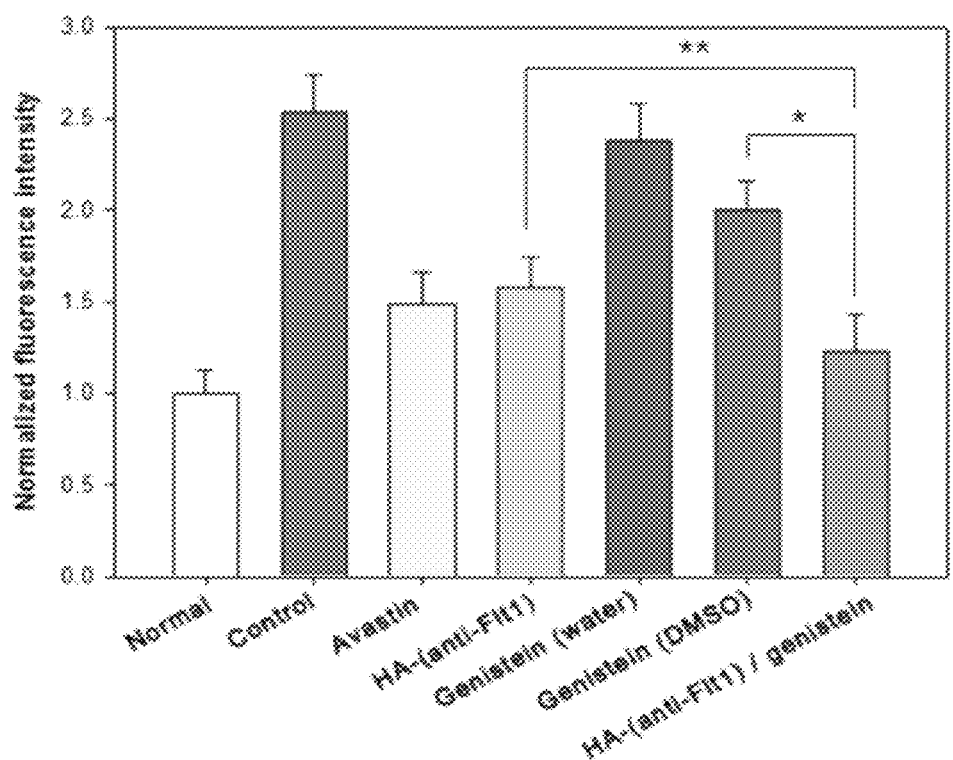

FIG. 23 is a view illustrating the effect of inhibiting vascular hyperpermeability due to diabetic retinopathy by the genistein-loaded, hyaluronic acid-peptide conjugate micelle. FIG. 23a is fluorescence microscopic images for the retinas of the normal control group, the negative control group (untreated), and the groups treated with Avastin, the hyaluronic acid-peptide conjugate (HA-(anti-Flt1)), genistein as dispersed in distilled water and DMSO, the genistein-loaded, and hyaluronic acid-peptide conjugate micelle (HA-(anti-Flt1)/genistein). FIG. 23b is a view illustrating the results of quantitatively analyzing the fluorescence intensity of retina as shown in FIG. 23a with Image J Program (*P=0.0002 and ** P=0.020, n=5).

Figure 24:
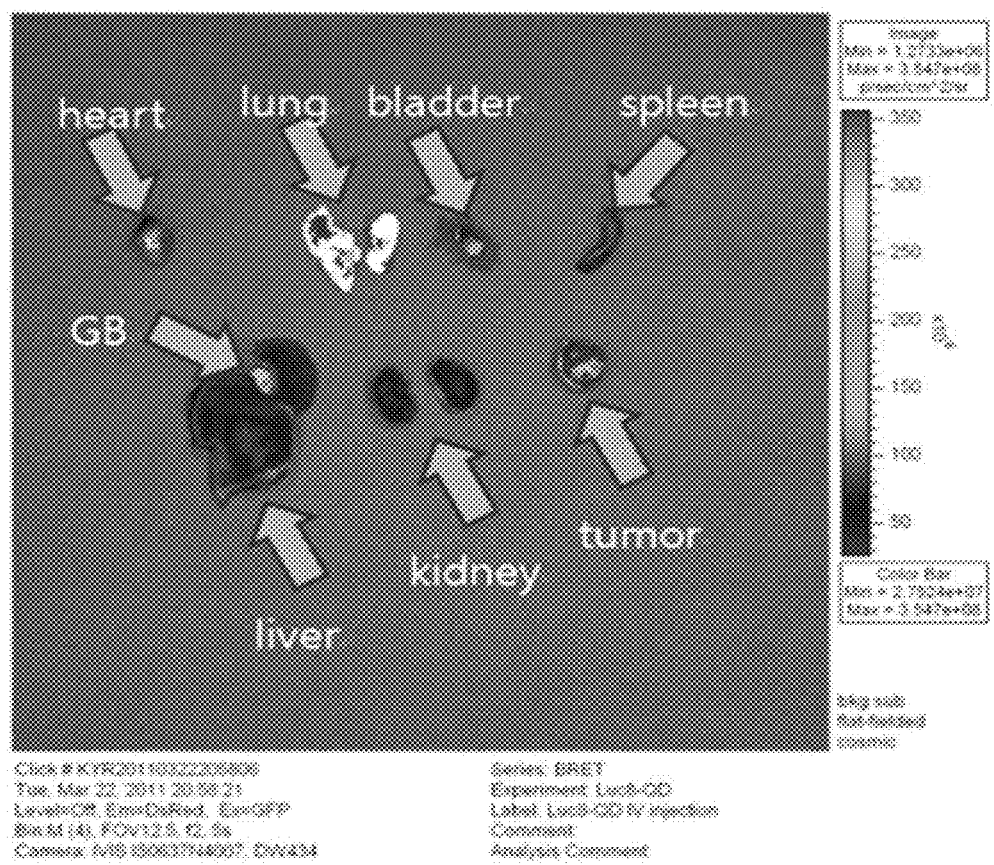

FIG. 24 is a view illustrating the evaluation through bioimaging as to the capacity of targeting tumor by using the doxorubicin-loaded, hyaluronic acid-peptide micelle. The fluorescence imaging gave the results that the micelles were accumulated onto the tumor tissue.

Figure 25:
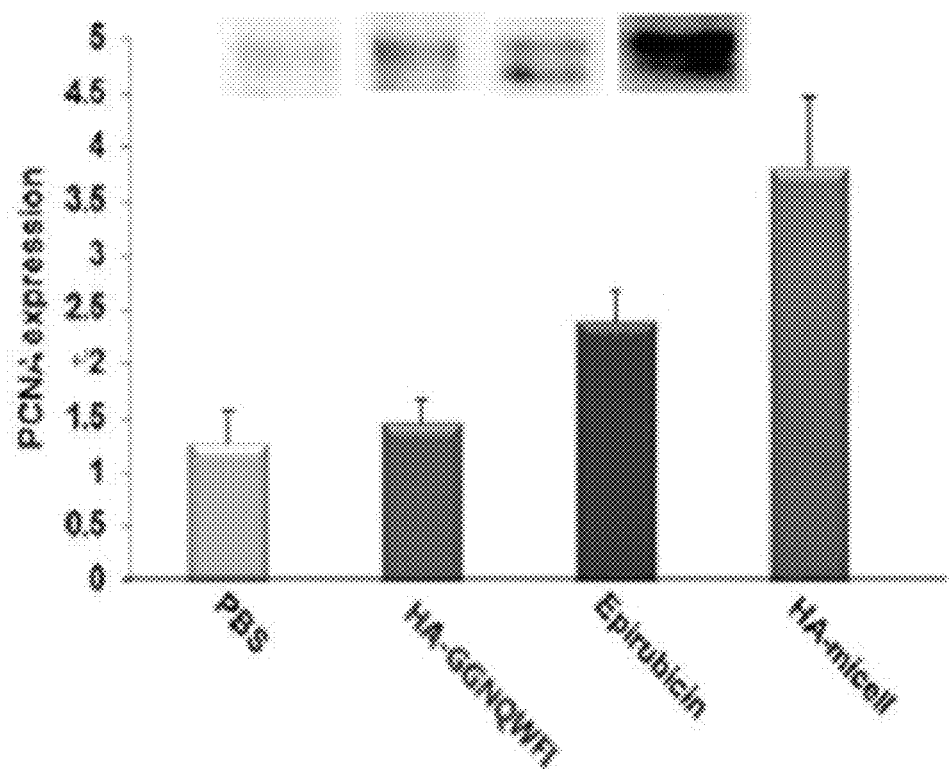

FIG. 25 is a view illustrating the results of western blot measuring the level of PCNA in the liver tissue by using the epirubicin-loaded, hyaluronic acid-peptide micelle of Example 4. This results confirm that the epirubicin-loaded, hyaluronic acid-peptide conjugate micelle has an anti-cancer effect superior to the other groups.

DETAILED DESCRIPTION OF THE EMBODIMENTS

In order to achieve the foregoing objectives, an embodiment of the present invention provides a drug delivery composition comprising a micelle consisting of a shell region comprising hyaluronic acid (HA) or a pharmaceutically acceptable salt thereof and a core region comprising a water-insoluble peptide with a terminal amine group, wherein the water-insoluble peptide is bound to said hyaluronic acid or its pharmaceutically acceptable salt; and a water-insoluble drug loaded inside the micelle.

Other embodiments of the present invention provide a method of producing a drug-loaded, hyaluronic-peptide conjugate micelle, which comprises the steps of:

reacting hyaluronic acid (HA) or its pharmaceutically acceptable salt with tetra-n-butyl ammonium hydroxide (TBA-OH) to prepare HA-TBA of Chemical Formula 1;

preparing a water-insoluble peptide with a terminal amine group;

reacting a carboxylic group of the prepared HA-TBA with the terminal amine group of the water-insoluble peptide in the presence of an organic solvent to prepare a hyaluronic acid-peptide conjugate micelle; and loading a water-insoluble drug into the prepared micelle.

Another embodiments of the present invention are to provide a method of delivering a drug by using a micelle that consists of a shell region comprising hyaluronic acid (HA) or a pharmaceutically acceptable salt thereof and a core region comprising a water-insoluble peptide with a terminal amine group, wherein the water-insoluble peptide is bound to said hyaluronic acid or its pharmaceutically acceptable salt.

[Chemical Formula 1]

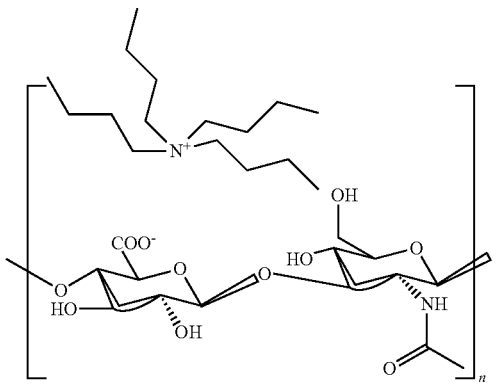

In Chemical Formula 1, n represents the number of the units per each molecule, which is an integer from 50 to 10,000.

Hereinafter, the drug delivery composition and the production method thereof according to an embodiment of the present invention will be explained in more detail.

In accordance with an embodiment of the present invention is provided a drug delivery composition comprising a micelle consisting of a shell region comprising hyaluronic acid (HA) or a pharmaceutically acceptable salt thereof and a core region comprising a water-insoluble peptide with a terminal amine group, wherein the water-insoluble peptide is bound to said hyaluronic acid or its pharmaceutically acceptable salt; and a water-insoluble drug loaded inside the micelle.

In accordance with other embodiments of the present invention is further provided a method of providing a drug-loaded, hyaluronic-peptide conjugate micelle, which comprises the steps of:

reacting hyaluronic acid (HA) or its pharmaceutically acceptable salt with tetra-n-butyl ammonium hydroxide (TBA-OH) to prepare HA-TBA of Chemical Formula 1;

preparing a water-insoluble peptide with a terminal amine group;

reacting a carboxylic group of the prepared HA-TBA with the terminal amine group of the water-insoluble peptide in the presence of an organic solvent to prepare a hyaluronic acid-peptide conjugate micelle; and loading a water-insoluble drug into the prepared micelle.

In accordance with another embodiments of the present invention is provided a method of delivering a drug by using a micelle that consists of a shell region comprising hyaluronic acid (HA) or a pharmaceutically acceptable salt thereof and a core region comprising a water-insoluble peptide with a terminal amine group, wherein the water-insoluble peptide is bound to said hyaluronic acid or its pharmaceutically acceptable salt.

The drug delivery method comprises the steps of preparing a micelle consisting of a shell region comprising hyaluronic acid (HA) or a pharmaceutically acceptable salt thereof and a core region comprising a water-insoluble peptide with a terminal amine group, wherein the water-insoluble peptide is bound to said hyaluronic acid or its pharmaceutically acceptable salt; filling the inside of the micelle with a drug; and administering the drug-loaded micelle to a subject in need of the drug.

Furthermore, the delivery of the drug can be preferably made in the form of a composition prepared by further comprising a proper carrier, an excipient, a diluent, and the like typically used in a medical composition in addition to the micelle.

In the drug delivery composition, the method of producing the drug-loaded, hyaluronic acid-conjugate micelle, and the drug delivery method by using the micelle according to the present invention, the biocompatible, biodegradable hyaluronic acid-peptide conjugate micelle is loaded with the water-insoluble drug (i.e., the active component), making it possible to be safely used for humans, and the water insoluble drug with a low bio-absorbability can be effectively dispersed in an aqueous solution such that its water solubility is greatly enhanced and the duration of the medicinal effect is extended. Therefore, the composition and the methods of the present invention can be widely utilized in the fields of drug delivery systems of a water-insoluble active ingredient including the water-insoluble drugs and the like.

Hyaluronic acid that forms a shell region corresponding to the outer shell of the micelle is a natural polymer with biocompatibility and biodegradability. Not only does it show hydrophilicity but also it has a functional group to which a hydrophobic moiety can be bound, and thus it can be properly used for forming the outer shell of the micelle.

Preferably, hyaluronic acid or its pharmaceutically acceptable salt can be a compound (HA-TBA) represented by Chemical Formula 1 as follows:

[Chemical Formula 1]

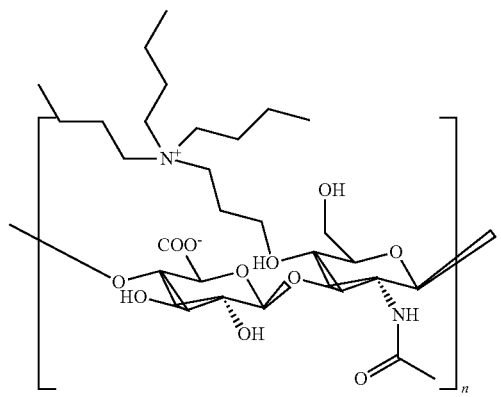

In Chemical Formula 1, n, representing the number of the units per one molecule, is an integer of 50 to 10,000.

Figure 1A:
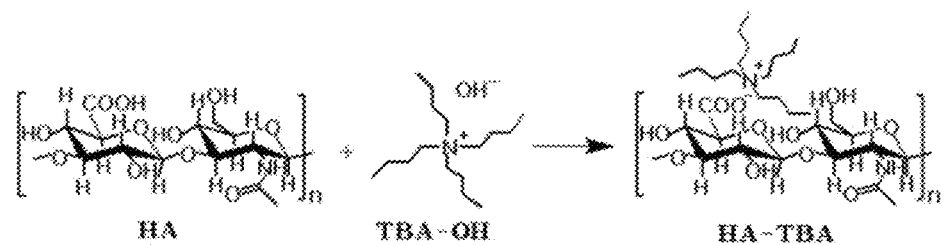
FIG. 1 schematically illustrates a chemical scheme as to the production method of the hyaluronic acid-peptide conjugate in accordance with an embodiment of the present invention (FIG. 1a: the step of preparing HA-TBA.
FIG. 1b: the step of preparing a hyaluronic acid-peptide conjugate by using HA-TBA), and the process of encapsulating a hydrophobic drug into the hydrophobic inner core of the hyaluronic acid-peptide conjugate micelle (FIG. 1c).
Figure 1B:
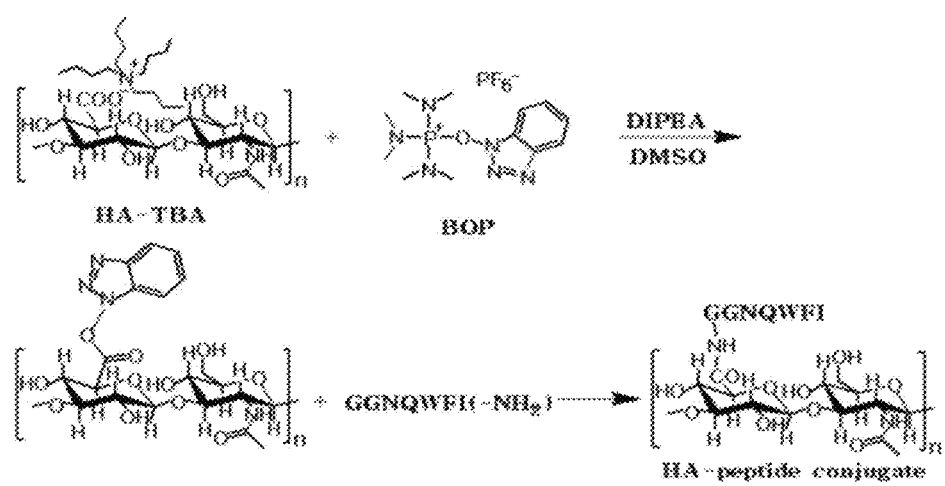

For illustration, FIG. 1 schematically shows a production method of the hyaluronic acid-peptide conjugate in accordance with an embodiment of the present invention. As shown in FIG. 1a, hyaluronic acid reacts with TBA-OH in an aqueous solution to form HA-TBA. After that, as shown in FIG. 1b, the HA-TBA and a water-insoluble peptide having a terminal amine group react in the presence of an organic solvent to provide a hyaluronic acid-peptide conjugate.

Figure 1C:
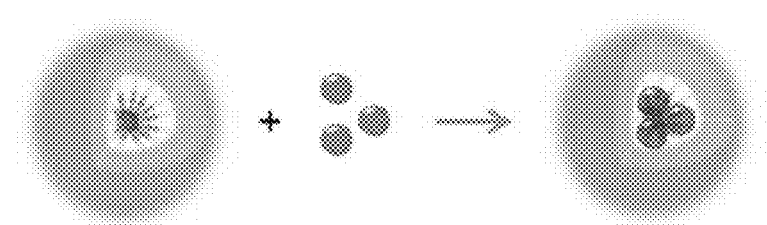

When being dispersed in an aqueous solution, the hyaluronic acid-peptide conjugate spontaneously forms a micelle due to the interaction of the hydrophobic core region in order to minimize contact with water and stabilize the free energy, and the outer shell region thus obtained brings about an increase in the solubility for the aqueous solution. Therefore, as shown in FIG. 1c, the hydrophobic inner core of the hyaluronic acid-peptide conjugate micelle can be loaded with a water-insoluble drug to provide a drug-loaded, hyaluronic acid-peptide conjugate micelle.

The water-insoluble drug has suffered drawbacks that due to its properties of neither being dissolved nor being dispersed in water, the drug shows a decreased bioavailability, failing to take its desired effect sufficiently, and its formulation process becomes difficult, as well. However, the present inventors have found that delivering the water-insoluble drug as it is loaded inside the micelle can greatly enhance its bioavailability and extend the duration of its medicinal effect. Moreover, the hyaluronic acid-peptide conjugate micelle has its own therapeutic effect from the peptide contained therein, which may act in combination with the drug loaded therein to further increase the entire therapeutic effect.

The hyaluronic acid (HA) or its pharmaceutically acceptable salt that can be used includes, but is not limited to, the one having a molecular weight of 10,000 to 3,000,000 Dalton (Da). The molecular weight within the foregoing range makes it possible for the hyaluronic acid or its pharmaceutically acceptable salt to be properly used for a conjugate for delivering a drug.

In the water-insoluble peptide with a terminal amine group, the amine group contained in the N-terminal of the peptide itself can be used without any additional preparation process. Furthermore, one can introduce and use an additional amine group at the C-terminal (containing no amine group) of the peptide or even at the N-terminal (containing an amine group with a lower reactivity) of the peptide. Even when the reactivity of the amine group is not really low, it is possible to introduce and use an additional amine group at the C-terminal or the N-terminal of the peptide for the purpose of obtaining better results.

The number of the amino acids composing the water-insoluble peptide is not particularly limited, and one can use even a protein. However, the higher the number of amino acids, the lower the number of the peptide linkable per one molecule of the hyaluronic acid or its pharmaceutically acceptable salt should be. Accordingly, it can preferably consist of 5 to 10 amino acid sequences, and preferably, can be the one including lysine or glycine at the C-terminal or the N-terminal.

Preparation of the water-insoluble peptide with a terminal amine group can be made without particular limitations, but it can be carried out by further introducing lysine or glycine to the C-terminal or the N-terminal of the peptide. When the amine group is introduced at the end of the peptide by using lysine or glycine, the introduced amine group may results in an enhanced conjugation reactivity.

In addition, the water-insoluble peptide with a terminal amine group can be selected with no limitation provided that it can be dissolved in an organic solvent without being dissolved in an aqueous solution. In particular, one can use anti-Flt1 peptide, the antagonist peptide against VEGFR1 (Flt 1) and preferably, it is possible to use at least one selected from the group consisting of GNQWFI(SEQ ID NO: 1), KGNQWFI (SEQ ID NO: 2), GGNQWFI (SEQ ID NO: 3). The anti-Flt1 peptide comprises tryptophan, phenyl alanine, and isoleucine, all of which are involved in the hydrophobic interaction upon the formation of the micelle and are highly hydrophobic even at a lower pH so that it can always form a micelle structure in the aqueous solution irrespective of a condition such as a temperature or a pH value.

In addition, the number of the water-insoluble peptide molecules to be bound preferably corresponds to an integer of 4 to 15% of the number of the units (an integer n=50 to 10,000) per a molecule of the compound (HA-TBA) of Chemical Formula 1. The hyaluronic acid-peptide conjugate with the number of the peptide molecules bound thereto falling within the above range can have a desired duration for the medicinal effect and a desired bioavailability. If the number is smaller than the lower limit of the above range, the hydrophobic interaction of the core region is insufficient so that the micelle may not be properly formed. If the number exceeds the upper limit of the above range, the conjugate undesirably has a decreased solubility in the aqueous solution.

In order to bond the water-insoluble peptides with the number of its molecules being in the above range, one can react the water-insoluble peptide in such a manner that the number of its molecules corresponds to an integer of 5 to 20% of the number of the units per one molecule of HA-TBA. If the number fails to reach the lower limit of the above range, the formation of the micelle may not be effectively achieved and the peptide may not sufficiently take its own pharmaceutical effect. If the numbers of the reacting peptide molecules exceed the upper limit of the above range, the reaction may occur but the conjugation efficiency would undesirably decrease.

The preparation of the HA-TBA can be carried out by using a cation exchange resin. Specifically, the preparation of the HA-TBA may comprise the steps of subjecting tetra-n-butyl ammonium hydroxide to a reaction with a cation exchange resin; and further adding and reacting hyaluronic acid (HA) or its pharmaceutically acceptable salt.

In this regard, it is possible to use any cation exchange resin with no limitation provided that it can react with tetra-n-butyl ammonium hydroxide to exchange its cation with the cation of TBA-OH.

Preferably, for the cation exchange resin, one can use at least one selected from the group consisting of Dowex 50WX2-200, Dowex 50WX4-400, Dowex 50WX2-100, Dowex 50WX2-400, Dowex 50WX8-100, Dowex 50WX8-200, and Dowex 50WX8-400. Forming the HA-TBA by using the foregoing cation exchange resin is advantageous in that the $Na^+$ ion in the carboxylic group of HA is exchanged with a TBA ion to convert HA-Na to HA-TBA.

The preparation of the hyaluronic acid-peptide conjugate micelle by reacting the carboxylic group of the HA-TBA with the terminal amine group of the water-insoluble peptide can proceed in an organic solvent.

In this regard, one can use any organic solvent with no limitation provided that it can dissolve the HA-TBA and the water-insoluble peptide. Specifically, one can use at least one selected from the group consisting of dimethyl sulfoxide (DMSO), dimethylformamide (DMF), dimethylacetamide, N-methyl-2-pyrrolidone (NMP), and hexamethylphosphoramide (HMPA).

Further, the preparation of the micelle may comprise further adding N,N-diisopropyl ethylamine (DIPEA), 2,2,6,6-tetramethylpiperidine, or a mixture thereof to carry out a reaction of the carboxylic group of the HA-TBA with the terminal amine group of the water-insoluble peptide.

Prior to carrying out the preparation of the micelle, the production method of the present invention may further comprise a step of activating the HA-TBA by adding it to at least one activator selected from the group consisting of Benzotriazole-1-yl-oxy-tris(dimethylamino) phosphonium hexafluorophosphate (BOP), 1,3-Dicyclohexylcarbodiimide (DCC), and 1,3-Diisopropylcarbodiimide (DIC).

The step of loading the hyaluronic acid-peptide conjugate micelle with a water-insoluble drug can be carried out in a solvent mixture of an aqueous solvent and an organic solvent.

Specifically, the loading of the water-insoluble drug may comprise the steps of dissolving the prepared micelle in an aqueous solvent to prepare a micelle solution; dissolving the water-insoluble drug in an organic solvent to prepare a water-insoluble drug solution; and mixing the micelle solution and the water-insoluble drug solution.

The hyaluronic acid-peptide conjugate micelle can be dissolved in the aqueous solvent at a concentration of between 0.5 mg/ml and 5 mg/ml, preferably between 0.5 mg/ml and 2 mg/ml. If the concentration of the conjugate in the aqueous solution is too high, exceeding the upper limit of the above range, dispersion of the micelle may deteriorate and agglomeration may undesirably occur.

Preferably, the water-insoluble drug is used in such an amount that it can be sufficiently dissolved in the organic solvent. Preferably, it can be dissolved at a concentration of between 0.5 mg/ml and 15 mg/ml, preferably between 0.5 mg/ml and 10 mg/ml with respect to the organic solvent. However, the present invention is not limited thereto, and depending on the types of the drug or the solvent, one can properly choose and use a drug in a suitable amount for being sufficiently dissolved in the organic solvent.

The organic solvent can be used without any limitation provided that it can dissolve the water-insoluble drug. Specifically, one can use at least one selected from the group consisting of dimethyl sulfoxide (DMSO), dimethylformamide (DMF), dimethylacetamide, N-methyl-2-pyrrolidone (NMP), hexamethylphosphoramide, (HMPA), ethanol, and chloroform.

The aqueous solvent can be water, distilled water, distilled water for injection, a physiological saline, a buffered solution (e.g., phosphate buffered solution), or the like.

The step of loading the water-insoluble drug to the hyaluronic acid-peptide conjugate micelle can be carried out, for example, by using a method of simply mixing the micelle solution and the water-insoluble drug solution, a sonication method, a mixing by a syringe pump, a solvent-substitution method by dialysis, an O/W emulsion method with using a volatile solvent.

Preferably, it can be carried out by using the sonication method, which comprises the steps of treating a mixed solution of the micelle solution with the hyaluronic acid-peptide conjugate dissolved therein and the water-insoluble drug solution at a temperature of 25 to 35° C. for 3 to 30 minutes.

Specifically, for filling of genistein, the sonication can be conducted for 20 to 30 minutes, and for filling of dexamethasone, doxorubicin, or epirubicin, it can be conducted for 3 to 10 minutes, more preferably 4 to 8 minutes. As such, the sonication time can vary with the types of the drug to be loaded for the purpose of increasing the loading efficiency.

Preferably, the micelle with the water-insoluble drug packing therein may have a diameter of 100 to 300 nm but the present invention is not limited thereto. With the diameter being in the above range, the micelle can be effectively introduced into the cells via receptor-mediated endocytosis while circulating in the blood. The diameter of the micelle can be determined through the measurement of a Dynamic Light Scattering (DLS) apparatus and the observation with a Transmission Electron Microscope (TEM).

For the water insoluble drug, one can select any drug with no limitation provided that it can be dissolved in the organic solvent without being dissolved in the aqueous solution.

Preferably, the water-insoluble drug can be an angiogenesis inhibitor, an inhibitor for vascular hyperpermeability due to diabetic retinopathy, an asthma drug, or an anti-cancer drug.

Preferably, the angiogenesis inhibitor is a drug having an effect of inhibiting the growth of the new blood vessel in the eyeball such as cornea or retina. Preferably, the anticancer drug can be for various cancers such as leukemia, bladder cancer, breast cancer, stomach cancer, lung cancer, ovarian cancer, thyroid cancer, and the like.

Preferably, it is possible to use genistein having an effect of inhibiting angiogenesis, dexamethasone having an effect of treating an inflammation, doxorubicin or epirubicin having an anticancer effect, but the present invention is not limited thereto.

Preferably, the micelle can be loaded with the water-insoluble drug in an amount of 0.1 to 70% by weight, more preferably 1 to 50% by weight with respect to the total weight of the micelle, in light of the administered amount of the hyaluronic acid-peptide conjugate effective for each disease and the effective dosage of the foregoing drugs.

The drug delivery composition of the present invention may further comprise a suitable carrier, an excipient, and a diluent typically used in the preparation of the medical composition.

For example, the carrier, the excipient, and the diluent can be lactose, dextrose, sucrose, sorbitol, mannitol, xylitol, erythritol, maltitol, starch, Akasia gum, alginate, gelatin, calcium phosphate, calcium silicate, cellulose, methyl cellulose, microcrystalline cellulose, polyvinyl pyrrolidone, water, methyl hydroxy benzoate, propyl hydroxy benzoate, talc, magnesium stearate, or the like.

The medical composition may be administered orally or parenterally in accordance with a typical method. For example, when being orally administered, it can be used as a formulation of a powder, a granule, a tablet, a suspension, an emulsion, a syrup, or the like. When being parenterally administered, it can be administered via an intravenous injection, a muscle injection, a subcutaneous injection, or the like. However, the present invention is not limited thereto and any possible route of administration can be adopted.

The preferred dosage can be any amount suitable for the treatment or the prevention of disease and/or for the subject to be administered. It can be adjusted depending on various factors such as the age, the sex, the physical conditions, and the body weight of the subject to be administered, the types and the severity of disease, the formulation types, the types and the content of other components contained in the composition, the secretion rate of the composition, and the route and the period of administration, all of which can be properly selected by a person of ordinary skill in the art.

The subject to be administered can be mammals including humans. When being translated into the amount of the drug contained in the drug-loaded micelle, the therapeutically effective amount (i.e., an effective dose) at a time can be, for example, from 1 to 5 mg of genistein for treating eye disease associated with angiogenesis (5 to 15 mg based on the conjugate wherein 10% of the units was conjugated with the peptide, and 1 to 5 mg based on the peptide content) per 1 kg of the adult's body weight and it can be administered at least one time. Furthermore, in case of treating asthma disease, the dexamethasone-loaded micelle can be administered via nasal cavity at a dose of 1 to 5 mg of dexamethasone (10 to 20 mg based on the peptide content) at least one time. However, the foregoing dosages are merely an example to illustrate the present invention, and these ranges should not limit the scope of the present invention.

As described above, the production method of the drug-loaded, hyaluronic acid-peptide conjugate micelle in accordance with an embodiment of the present invention can be carried out in a solvent mixture of the aqueous solution and the organic solvent so that it can be applied for the preparation of the drug delivery system for the water-insoluble medicine that can be dissolved in the organic solvent.

According to the drug delivery composition and the production method of the drug-loaded, hyaluronic acid-peptide conjugate micelle, the reaction for loading can proceed on a mixed solvent of an aqueous solvent and an organic solvent. Therefore, the present invention can be applied for various types of water-insoluble active components and a biocompatible and biodegradable derivative is loaded with a drug to provide a drug-loaded micelle, which is safe to be utilized for human bodies. Moreover, the micelle has a therapeutic effect resulting from the peptide contained therein, which can act in combination with the drug loaded inside the micelle.

The drug delivery composition and its production method of the present invention can be utilized in the field of producing the sustained release formulation of a water-insoluble medicine with an extended duration of the medicinal effect.

Hereinafter, various examples of the present invention will be explained. However, these examples are presented as the illustration of the present invention and the scope of the invention should not be construed to be defined thereby.

PREPARATION EXAMPLE 1

Preparation of Hyaluronic Acid-Peptide Conjugate (GNQWFI)

After 12.5 g of Dowex 50WX-8-400 ion-exchange resin was washed with 250 mL of distilled water three times, the Dowex resin was put into 24.5 mL of tetra-n-butyl ammonium hydroxide (TBA-OH) and reacted for 30 minutes, and then the resulting resin was filtered through a filter. 1 g of hyaluronic acid (HA) (MW=100 kDa) was dissolved in 100 mL of distilled water and to the resulting solution was added 10 g of the DOWEX-TBA resin obtained as above and reacted for 3 hours. The supernatant was filtered through a 0.45 μm filter and freeze-dried for 3 days to give a HA-TBA derivative.

Then, after 132.8 mg of the HA-TBA derivative was dissolved in 16 ml of dimethyl sulfoxide (DMSO) (based on the case where 20 mg of peptide was reacted with the 100.5%-substituted HA-TBA at 25 peptides per a molecule), Benzotriazole-1-yloxy-tris(dimethylamino)phosphonium hexafluorophosphate (BOP) was added thereto in an amount of 2.5 molar times with respect to the HA-unit and the mixture thus obtained was stirred for 30 minutes, resulting in the activation of the carboxylic group of HA. Likewise, after 20 mg of a water-insoluble peptide having a terminal amine group (anti-Flt1 peptide) GNQWFI(SEQ ID NO: 1) was dissolved in 4 ml of DMSO, the resulting solution was mixed with the HA-TBA solution prepared as above. To the resulting mixture was added N,N-diisopropyl ethylamine (DIPEA) in the same molar amount as the HA unit, and reacted overnight. Then, to the reaction solution was added the same volume of 1M NaCl aqueous solution, and the pH of the resulting solution was lowered to 3.0 and raised to 7.0 for the termination of the reaction. The solution was subjected to a dialysis against an excess amount of 100 mM NaCl aqueous solution, 25% (v/v) ethanol, and distilled water, and then was freeze-dried for 3 days to provide a hyaluronic acid-peptide conjugate with a lower peptide content wherein 20 peptides were conjugated to one molecule of the HA-TBA.

Further, a hyaluronic acid-peptide conjugate with a higher peptide content (wherein 28 peptides were conjugated to one molecule of the HA-TBA) was obtained in the same manner as described above, except that the amount of the water-insoluble peptide dissolved in DMSO was made to be 28 mg (i.e., reacting 35 peptides per a molecule of the HA-TBA).

PREPARATION EXAMPLE 2

Preparation of Hyaluronic Acid-Peptide Conjugate (KGNQWFI)

Hyaluronic acid-peptide conjugates with a lower peptide content and a higher peptide content were obtained in the same manner as set forth in Preparation Example 1 except for using a peptide with a terminal amine group having a better reactivity to the carboxylic group of hyaluronic acid (KGNQWFI) (SEQ ID NO: 2) prepared by introducing lysine (K) into the end of the anti-Flt1 peptide having a sequence of GNQWFI (SEQ ID NO: 1).

PREPARATION EXAMPLE 3

Preparation of Hyaluronic Acid-Peptide Conjugate (GGNQWFI)

Hyaluronic acid-peptide conjugates with a lower peptide content and a higher peptide content were obtained in the same manner as set forth in Preparation Example 1 except for using a peptide with a terminal amine group having a better reactivity to the carboxylic group of hyaluronic acid (GGNQWFI) (SEQ ID NO: 3) prepared by introducing glycine (G) into the end of the anti-Flt1 peptide having a sequence of GNQWFI (SEQ ID NO: 1).

The characterization of the hyaluronic acid-peptide (GGNQWFI) conjugate obtained from Preparation Example 3 was conducted by using $^1$H-NMR (DPX500, Bruker, Germany) and a spectrofluorometer (Cary Eclipse Fluorescence Spectrophotometer, Varian, Australia)

EXPERIMENTAL EXAMPLE 1

NMR Analysis of Hyaluronic Acid-Peptide Conjugate 1-1) Analysis method

Figure 2A:
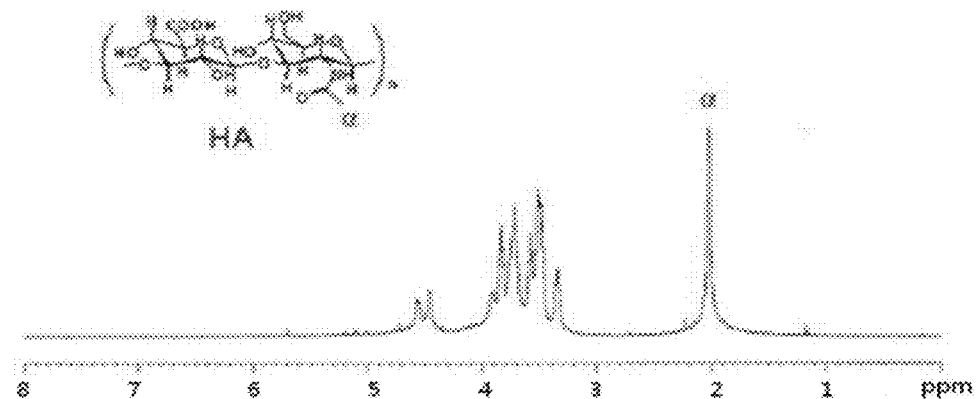
FIG. 2 is $^1$H-NMR spectra of hyaluronic acid (FIG. 2a) and the hyaluronic acid-peptide conjugate of Preparation Example 3 (FIG. 2b).

The hyaluronic acid-peptide conjugate with a lower peptide content as obtained from Preparation Example 3 (HA-GGNQWFI) was analyzed with $^1$H-NMR (DPX500 or DPX300, Bruker, Germany). $^1$H-NMR spectrums of HA and the hyaluronic acid-peptide conjugate as obtained from Preparation Example 3 were shown in FIGS. 2a and 2b.

1-2) Results of Analysis

Figure 2B:
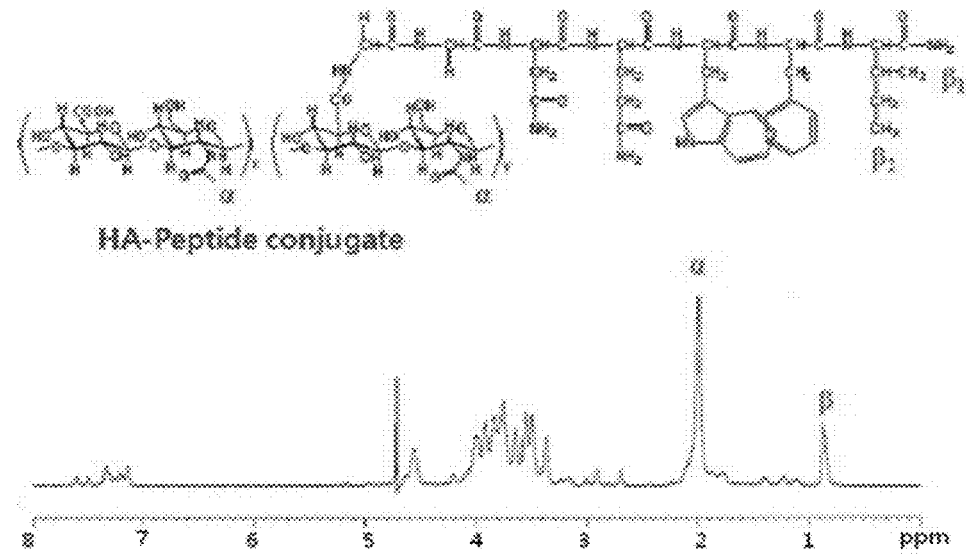

As shown in FIG. 2b, $^1$H-NMR spectrum for the hyaluronic acid-peptide (GGNQWFI) conjugate as obtained from Preparation Example 3 includes not only the peak for hyaluronic acid but also the peaks for the peptide. In particular, the peak at d=7.10~7.65 ppm is due to the presence of the aromatic rings of phenylalanine and tryptophan, and the peak of d=0.866 ppm is due to the presence of two methyl groups of isoleucine. For a quantitative analysis, the methyl resonance of the acetamido moiety of HA at d=1.85~1.95 ppm was chosen as an internal standard ('a' of FIG. 2a and FIG. 2b). The peptide content of the hyaluronic acid-peptide conjugate of Preparation Example 3 was calculated by comparison between the peak area at d=1.85~1.95 ppm and the peak area at d=0.866 ppm (See, 'β' of FIG. 2b). $^1$H-NMR spectrum analysis confirmed the synthesis of the hyaluronic acid-peptide conjugate.

EXPERIMENTAL EXAMPLE 2

Fluorescence Analysis of Hyaluronic Acid-Peptide Conjugate

1) Determination of a Standard Curve for Tryptophan for a Fluorescence Analysis

In order to find out whether the hyaluronic acid-peptide conjugate is formed or not through the fluorescence analysis of the hyaluronic acid-peptide conjugate, phenylalanine, tryptophan, anti-Flt1 peptide (GGNQWFI) (SEQ ID NO: 3), and the hyaluronic acid-peptide conjugate (HA-GGNQWFI) with a lower peptide content of Preparation Example 3 were dissolved in 0.5 M HCl, respectively. After being subject to excitation at 280 nm, the photoluminescence of each sample was measured by a spectrofluorometer (Cary Eclipse Fluorescence Spectrophotometer, Varian, Australia). The results are shown in FIG. 3a.

Figure 3A:
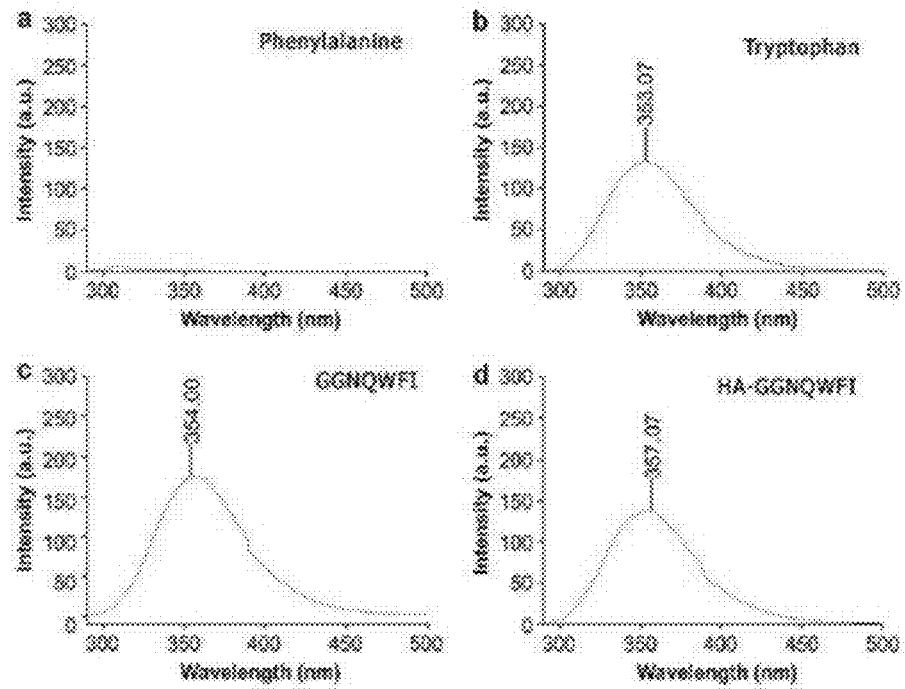
FIG. 3a illustrates the results of fluorescence analysis of phenyl alanine, tryptophan, anti-Flt1 peptide (GGNQWFI) (SEQ ID NO: 3), and the hyaluronic acid-peptide conjugate of Preparation Example 3.

As can be seen in FIG. 3a, while phenylalanine as subjected to excitation at 280 nm gave no fluorescence, tryptophan showed a sharp emission peak at 350 nm. The anti-Flt1 peptide (GGNQWFI) (SEQ ID NO: 3) and the hyaluronic acid-peptide conjugate as obtained from Preparation Example 3 yielded a sharp emission peak at 350 nm and there was no difference between the emission patterns prior to and after the conjugation.

In other words, among the amino acids composing anti-Flt1 peptide, tryptophan was found to maintain its original structure and its original fluorescence characteristics without any significant modification after the bioconjugation, and based on this finding, the standard curve for tryptophan was determined for the fluorescence analysis of the hyaluronic acid-peptide conjugate and utilized for a quantitative analysis in the following examples.

Figure 3B:
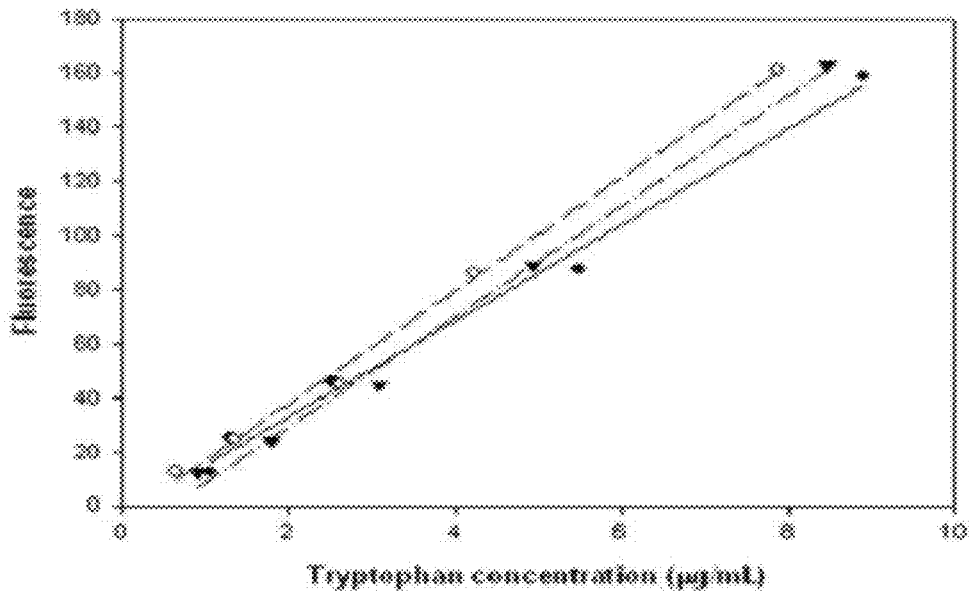
FIG. 3b illustrates the fluorescence standard curve for tryptophan.

Specifically, a tryptophan stock solution was prepared at a concentration of 6.4 mg/mL in 0.5M HCl, and then it was diluted to give tryptophan stock solutions at a concentration of 0.5, 1, 2, 4, and 8 μg/mL, respectively. With using each of the diluted tryptophan stock solutions at different concentrations (n=3), it was possible to plot a standard curve illustrating the fluorescence intensities depending on the concentration. (see, FIG. 3b)

2) Determination of Bioconjugation Efficiency Depending on the Types of the Amino Acid as Used for Introducing a Terminal Amine Group of a Peptide After 0.5 mg of the hyaluronic acid-peptide conjugates with a lower peptide content in accordance with Preparation Examples 1 to 3 were dissolved in 3 mL of 0.5M HCl and subjected to excitation at 280 nm, respectively, the photoluminescence of each sample was measured by a spectrofluorometer (Cary Eclipse Fluorescence Spectrophotometer, Varian, Australia). The results were quantitatively analyzed through a tryptophan fluorescence analysis and were shown in FIG. 4.

Figure 4:
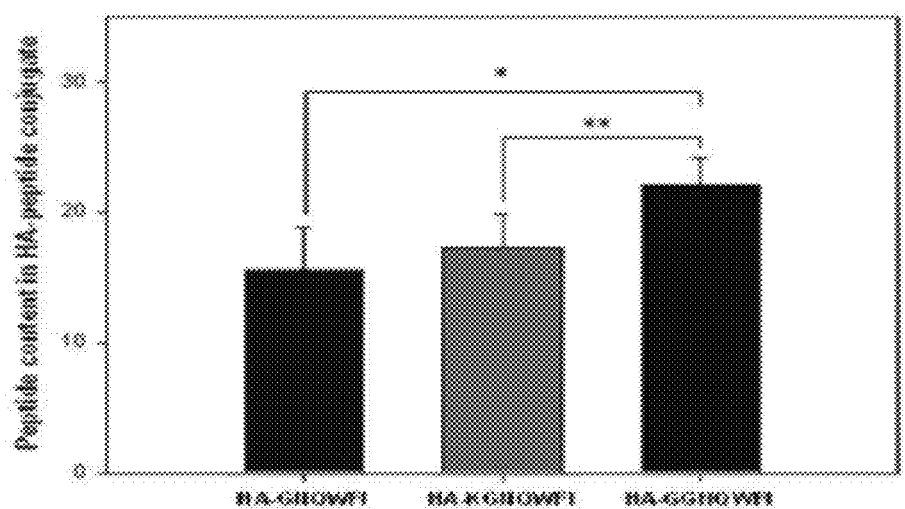
FIG. 4 illustrates the peptide contents (bioconjugation efficiency) in the hyaluronic acid-peptide conjugate depending on the types of the amino acids as used for the introduction of the terminal amine group of the peptide (* P=0.046 and ** P=0.070).

As shown in FIG. 4, the conjugate of Preparation Example 2 (HA-KGNQWFI) prepared by introducing lysine at the end of GNQWFI (SEQ ID NO: 1) and subjecting (KGNQWFI) (SEQ ID NO: 2) to a conjugation reaction was found to have an average bioconjugation efficiency increasing by 10% in comparison with that of the conjugate prepared without introducing lysine (Preparation Example 1: HA-GNQWFI). Meanwhile, the conjugate of Preparation Example 3 (HA-GGNQWFI) prepared by introducing glycine into at the end of GNQWFI(SEQ ID NO: 1) and subjecting (GGNQWFI) (SEQ ID NO: 3) to a conjugation reaction was found to have an average bioconjugation efficiency increasing by 40% in comparison with that of the conjugate of Preparation Example 1 prepared without introducing glycine. Therefore, in the following Examples and Experimental examples were used GGNQWFI (SEQ ID NO: 3) showing the highest bioconjugation efficiency and the HA-conjugate of Preparation Example 3 with a lower content of peptide, wherein 20 of said peptides were conjugated per one molecule of the HA-TBA.

3) Analysis for the Peptide Content in the Hyaluronic Acid-Peptide Conjugate and the Bioconjugation Efficiency Thereof The content of the bound peptides to the hyaluronic acid-peptide conjugate according to Preparation Example 3 was obtained by measuring the fluorescence intensity at an excitation wavelength of 280 nm and an emission wavelength of 350 nm and was quantitatively analyzed through an analysis of tryptophan fluorescence. The results were illustrated in FIG. 5 together with the results of analyzing the bioconjugation efficiency.

Figure 5:
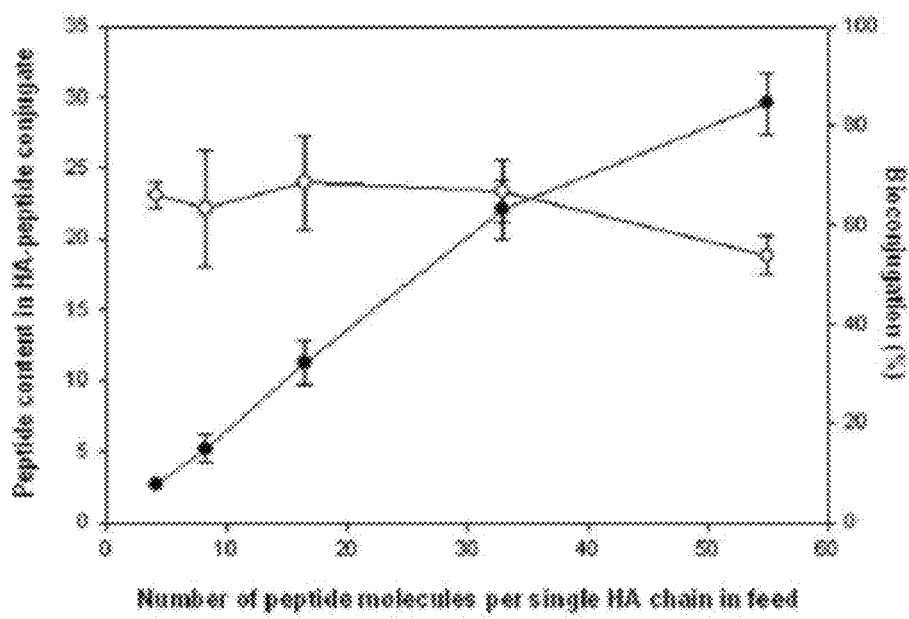
FIG. 5 shows the number of the peptide molecules bound to one hyaluronic acid chain in the hyaluronic acid-peptide conjugate of Preparation Example 3 (○) and its bioconjugation efficiency (○).

As shown in FIG. 5, the peptide content in the hyaluronic acid-peptide conjugate increased with increasing the number of the peptides as reacted per one molecule of HA. With changing the number of peptide molecules reacted per one molecule of HA in a feed into 4, 8, 16, 33, and 55, the average molecular number of the peptides bound per one molecule of HA was able to be controlled between 3 to 30. The bioconjugation efficiency (%) was denoted as a molar ratio of the peptide as reacted with respect to the peptide added to the reaction solution. When the number of the peptide molecules as reacted per one molecule of HA in a feed was no more than 33, the bioconjugation efficiency was constant at 65%. When the number of the peptides as reacted per molecule of HA in a feed was 55, the bioconjugation efficiency decreased to 53%.

EXPERIMENTAL EXAMPLE 3

Characterization of the Hyaluronic Acid-Peptide Conjugate Micelle 3-1) Analysis Method The anti-Flt1 peptide (GGNQWFI) (SEQ ID NO: 3) and the hyaluronic acid-peptide conjugate with a lower peptide content as prepared from Preparation Example 3 were dissolved in 4004, of PBS to have a final peptide concentration of 1.25 mg/mL, respectively. The amount of the anti-Flt1 peptide contained in each solution was measured with a changeable UV transilluminator (DUT-260, Core Bio System, Korea) by using 312 nm of light source. The formation of the hyaluronic acid-peptide micelle in an aqueous solution was confirmed by using a transmission electron microscope (TEM) (Hitachi, Tokyo, Japan). For a TEM analysis, 10 μL of the hyaluronic acid-peptide conjugate solution was dropped onto a 300 mesh copper TEM grid with a carbon film and then was dried. The average particle size was calculated out from the diameters obtained from the images of 30 particles.

In addition, the hydrodynamic diameter of the hyaluronic acid-peptide conjugate micelle was analyzed with a dynamic light scattering (DLS) apparatus (Zetasizer Nano, Malvern Instrument Co., UK) to confirm whether the micelle was formed depending on the number of the peptide molecules. Specifically, the hyaluronic acid-peptide conjugate prepared in the same manner as set forth in Preparation Example 3 except for the number of the conjugated peptide molecules was dissolved in an aqueous solution at a concentration of 1 mg/ml and put into PMMA cell to measure the distribution depending upon the hydrodynamic diameter.

3-2) Results of the Analysis

Figure 6A:
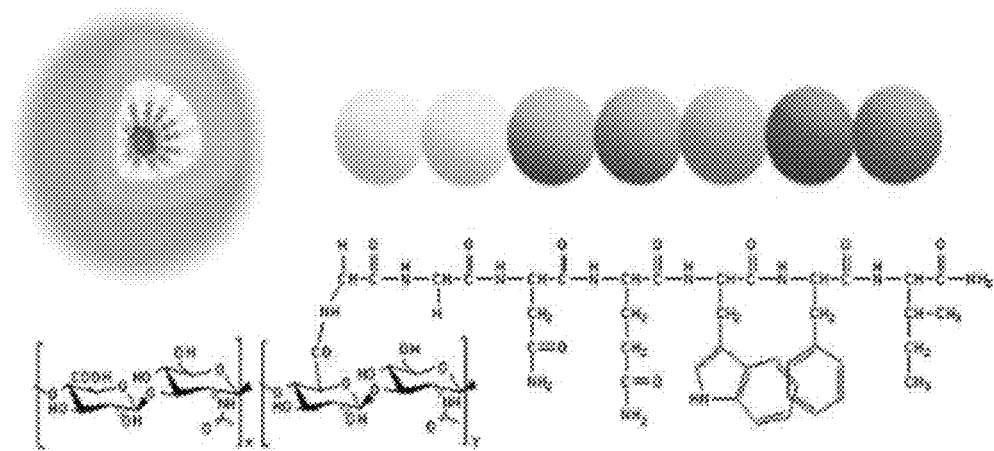
FIG. 6a is a view schematically illustrating the chemical structure of the hyaluronic acid-peptide conjugate of Preparation Example 3 and the structure of the hyaluronic acid-peptide conjugate micelle.

As shown in FIG. 6a, anti-Flt1 peptide (GGNQWFI) (SEQ ID NO: 3) had both of the hydrophilic moiety (GNQ) and the hydrophobic moiety (WFI). Therefore, when the anti-Flt1 peptide was bound to hyaluronic acid, the hydrophobic portion of the anti-Flt 1 peptide formed the hydrophobic inner core while hyaluronic acid formed the hydrophilic outer shell, resulting in the formation of the micelle structure as schematically shown in FIG. 6a.

Figure 6B:
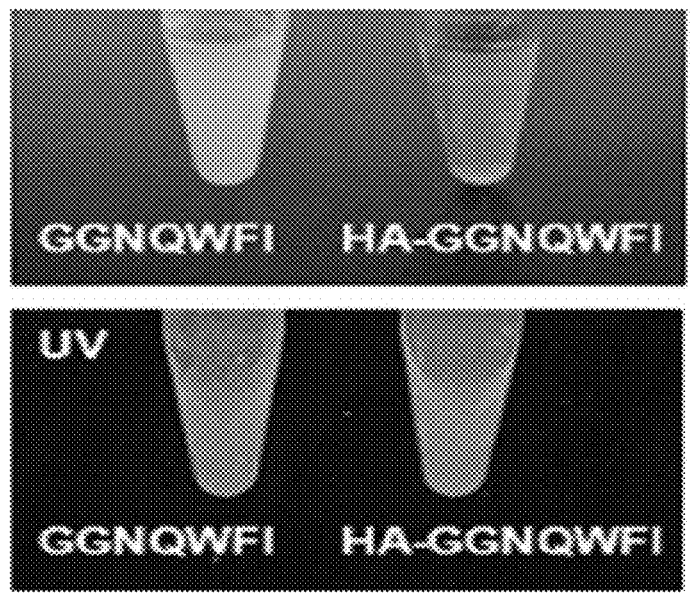
FIG. 6b is photographs taken of the solution of anti-Flt1 peptide (GGNQWFI) (SEQ ID NO: 3) and the solution of the hyaluronic acid-peptide conjugate of Preparation Example 3 under a visible light (upper one) and a UV light (lower one).

As shown in FIG. 6b, since the anti-Flt1 peptide was water-insoluble, it became turbid when being in the aqueous solution. However, the hyaluronic acid-peptide conjugate obtained by Preparation Example 3 became clear in the aqueous solution due to its highly-enhanced water solubility. However, as seen under UV rays, both solutions exhibited the same extent of fluorescence and this confirmed that they contained the same amount of the anti-Flt1 peptide.

Figure 6C:
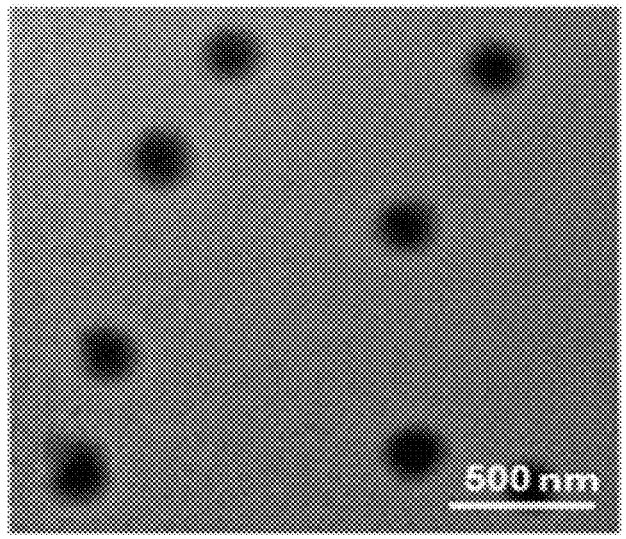
FIG. 6c is a TEM image of the hyaluronic acid-peptide conjugate micelle.

As shown in FIG. 6c, when the hyaluronic acid-peptide conjugate was observed with a transmission electronic microscope (TEM), it was present as a spherical particle with an average diameter of 234.5±20.6 nm (n=30).

Figure 6D:
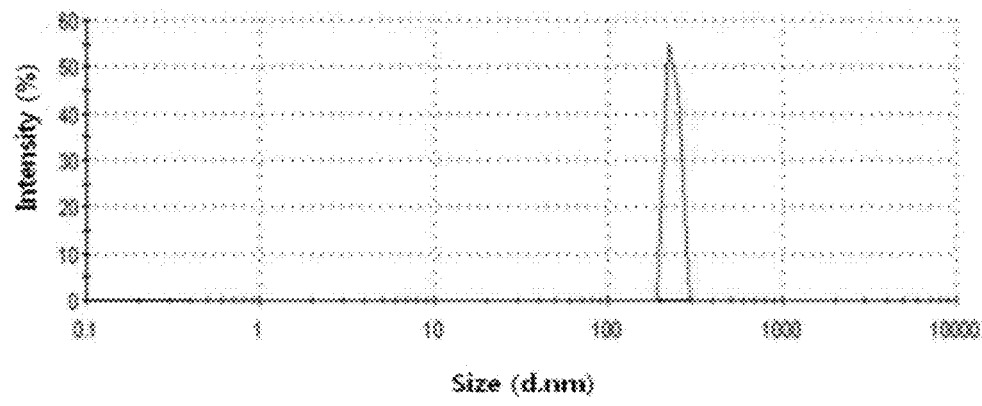
FIG. 6d is a view illustrating the results of DLS when 25 peptides being conjugated per one molecule of HA-TBA.
Figure 6E:
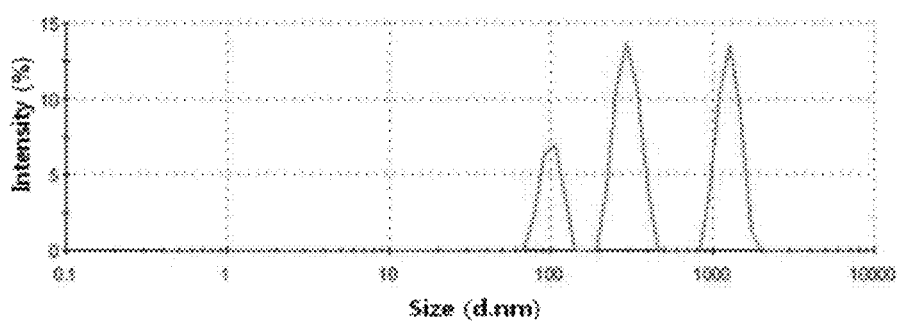
FIG. 6e is a view illustrating the results of DLS when 6 peptides being conjugated per one molecule of HA-TBA.

As shown in FIG. 6d and FIG. 6e, in the conjugate with 25 peptides per one HA-TBA molecule being conjugated thereto, one peak was observed at 222.0±8.5 nm (n=5) such that the formation of the micelle could be confirmed. However, in the conjugate with 6 peptides per one HA-TBA molecule being conjugated thereto, several peaks were observed in different positions, indicating that the micelle structure was not formed. Therefore, it can be confirmed that the number of the peptide molecules bound per one HA-TBA molecule has an effect on the formation of the micelle structure. Specifically, the formation of the micelle was confirmed in case of the conjugate wherein at least 12 peptide molecules were conjugated per one HA-TBA molecule, while no formation of the micelle was found in case of the conjugate wherein no more than 6 peptide molecules were conjugated. (for this, no data was illustrated)

EXAMPLE 1

Preparation of the Genistein-Loaded Hyaluronic Acid-Peptide Conjugate Micelle

After 1 mg of the hyaluronic acid-peptide (GGNQWFI) conjugate with a lower peptide content as prepared from Preparation Example 3 was dissolved in 0.8 ml of PBS and 0.5 mg of genistein was dissolved in 0.2 ml of DMSO, both solutions were mixed and sonicated (JAC 2010, KODO, Korea) in a water bath at a temperature of 30° C. for 25 minutes. Then, the reaction solution as sonicated was dialyzed against an excess amount of PBS to provide a genistein-loaded, hyaluronic acid-peptide conjugate.

EXAMPLE 2

Preparation of the Dexamethasone-Loaded Hyaluronic Acid-Peptide Conjugate Micelle After 1 mg of the hyaluronic acid-peptide (GGNQWFI) conjugate with a lower peptide content as prepared from Preparation Example 3 was dissolved in 1 ml of distilled water and 0.5 mg of dexamethasone was dissolved in 0.2 ml of ethanol, both solutions were mixed and sonicated (JAC 2010, KODO, Korea) in a water bath at a temperature of 30° C. for 6 minutes. Then, the reaction solution as sonicated was dialyzed against an excess amount of PBS to provide a dexamethasone-loaded, hyaluronic acid-peptide conjugate micelle.

EXAMPLE 3

Preparation of the Doxorubicin-Loaded Hyaluronic Acid-Peptide Conjugate Micelle

After 1 mg of doxorubicin.HCl was dissolved in 0.5 ml of distilled water, 0.5 ml of chloroform and 1 µl of triethanolamine (TEA) was added to the resulting solution, causing separation in layers to occur. 2 mg of the hyaluronic acid-peptide (GGNQWFI) conjugate with a lower peptide content as prepared from Preparation Example 3 was dissolved in 1 ml of PBS, and the resulting solution was mixed with 0.1 ml of the lower solution separated as above and then was subjected to tip-sonication by using Digital Sonifier 500 (Fisher Scientific) at 100 W for 5 minutes. Then, the reaction solution as sonicated was stirred overnight in the air to remove chloroform and dialyzed against an excess amount of PBS to provide a doxorubicin-loaded hyaluronic acid-peptide conjugate micelle.

EXAMPLE 4

Preparation of the Epirubicin-Loaded, Hyaluronic Acid-Peptide Conjugate Micelle with Epirubicin Loaded Therein After 1 mg of epirubicin. HCl was dissolved in 0.5 ml of distilled water, 0.5 ml of chloroform and 1 µl of triethanolamine (TEA) was added to the resulting solution, causing separation in layers to occur. 2 mg of the hyaluronic acid-peptide (GGNQWFI) conjugate with a lower peptide content as prepared from Preparation Example 3 was dissolved in 1 ml of PBS, and the resulting solution was mixed with 0.1 ml of the lower solution separated as above and then was subjected to tip-sonication by using Digital Sonifier 500 (Fisher Scientific) at 100 W for 5 minutes. Then, the reaction solution as sonicated was stirred overnight in the air to remove chloroform and was dialyzed against an excess amount of PBS to provide an epirubicin-loaded, hyaluronic acid-peptide conjugate micelle.

EXPERIMENTAL EXAMPLE 4

Characterization of the Drug-Loaded Hyaluronic Acid-Peptide Conjugate Micelle 4-1) Analysis Method The genistein-loaded hyaluronic acid-peptide conjugate micelle and the dexamethasone-loaded hyaluronic acid-peptide conjugate micelle as obtained from Examples 1 and 2 were analyzed with High Performance Liquid Chromatography (HPLC). The system for analysis is the same as follows: Waters 1525 binary HPLC pump, Waters 2487 dual λ absorbance detector, Waters 717 plus auto-sampler, and Waters Symmetry 300 C18 column. The mobile phase was 73 vol % 50 mM ammonium formate/27 vol % acetonitrile (ACN). The flow rate was 1 mL/min and the measurement wavelength was 260 nm.

The doxorubicin-loaded, hyaluronic acid-peptide conjugate micelle and epirubicin-loaded, hyaluronic acid-peptide conjugate micelle as obtained from Examples 3 and 4 were analyzed with UV spectrophotometer at a wavelength of 490 nm.

For a transmission electron microscope (TEM) (Hitachi, Tokyo, Japan) analysis, 10 μL of the solution of the drug-loaded, hyaluronic acid-peptide conjugate micelle was dropped onto a 300 mesh copper TEM grid with a carbon film and then was dried.

The hydrodynamic diameter of the drug-loaded hyaluronic acid-peptide conjugate micelle was analyzed with a dynamic light scattering (DLS) apparatus (Zetasizer Nano, Malvern Instrument Co., UK)

4-2) Analysis Results

The analysis made by High-Performance Liquid Chromatography (HPLC) or the UV spectrophotometer confirmed that genistein, dexamethasone, doxorubicin, and epirubicin encapsulated inside the hyaluronic acid-peptide conjugate micelles, respectively, and the loading efficiency for each drug was measured.

Figure 7A:
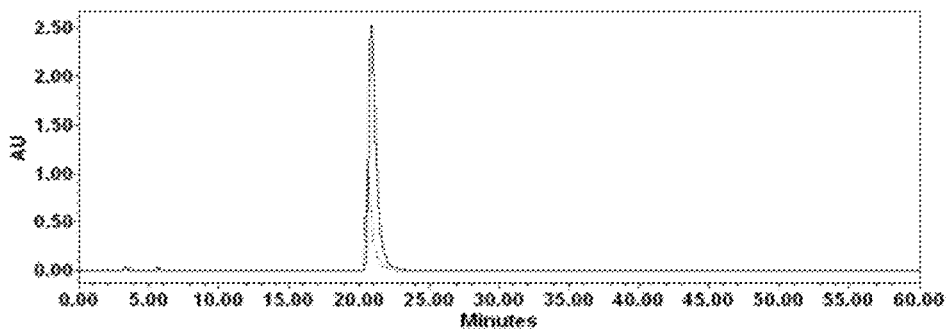
FIG. 7 is a view illustrating the measurement results of High Performance Liquid Chromatography of genistein (FIG. 7a) and dexamethasone (FIG. 7b) wherein the solid line represents the results for a mixed solution of the conjugate and the hydrophobic drug prior to the purification and the dotted line represents the results obtained after the purification of the drug as unloaded.
FIG. 7c is a view illustrating a UV spectrum of doxorubicin.
Figure 8A:
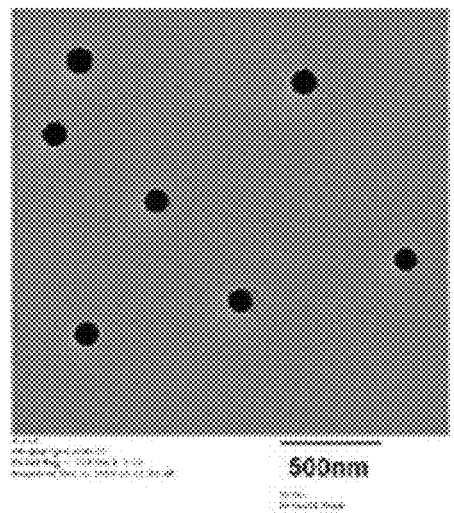
FIG. 8 is TEM images for the hyaluronic acid-peptide conjugate micelles, each of which is loaded with genistein (FIG. 8a), dexamethasone (FIG. 8b), doxorubicin (FIG. 8c), and epirubicin (FIG. 8d), respectively.
Figure 8A:
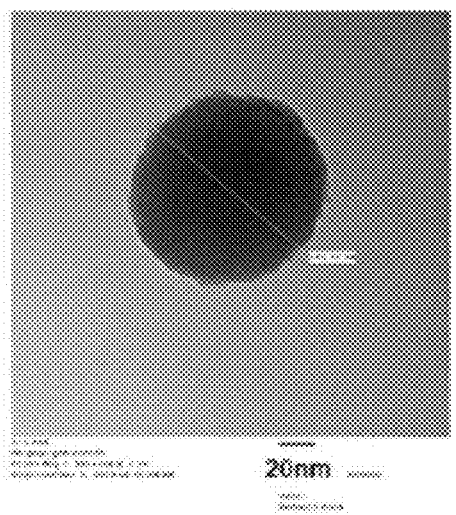
Figure 8B:
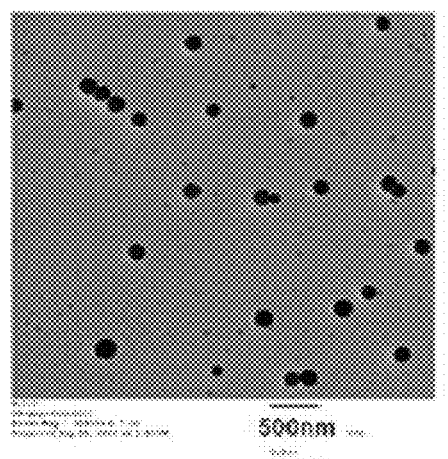
Figure 8B:
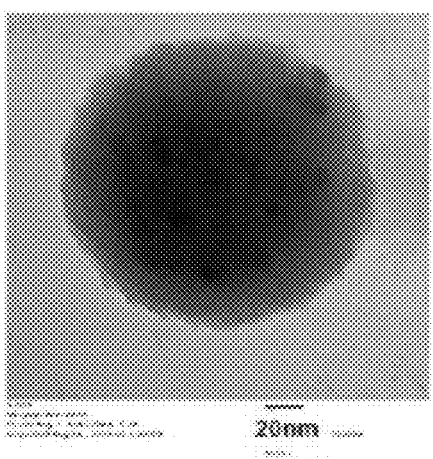
Figure 8C:
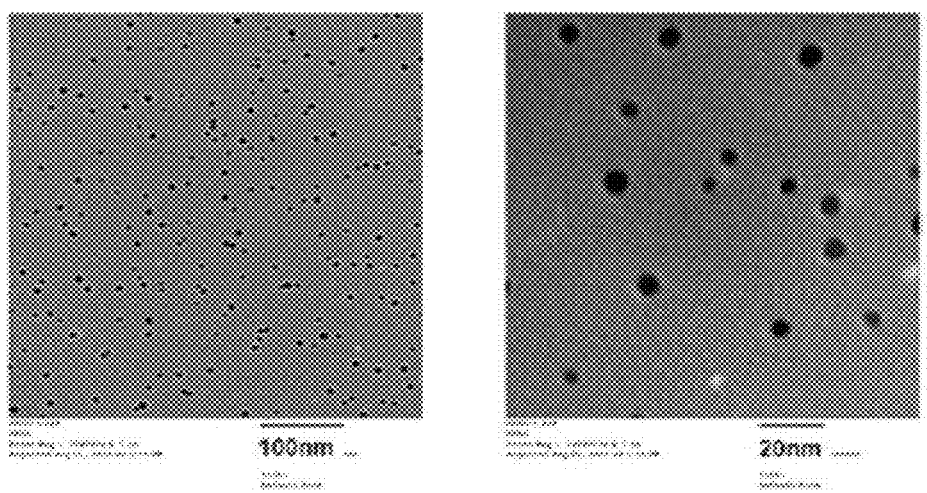
Figure 8D:
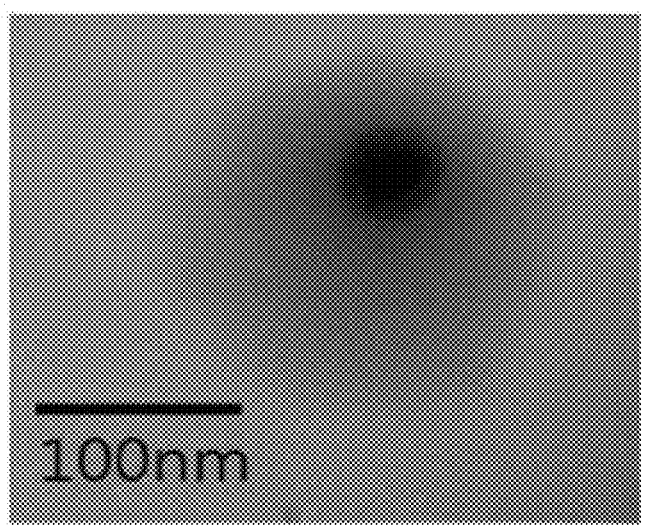
Figure 9A:
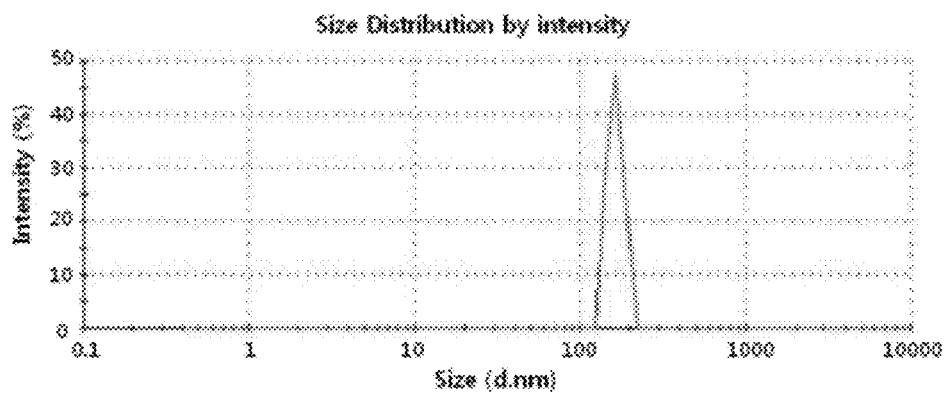
FIG. 9 is DLS images for the hyaluronic acid-peptide conjugate micelles, each of which is loaded with genistein (FIG. 9a), dexamethasone (FIG. 9b), doxorubicin (FIG. 9c), and epirubicin (FIG. 9d), respectively.
Figure 9B:
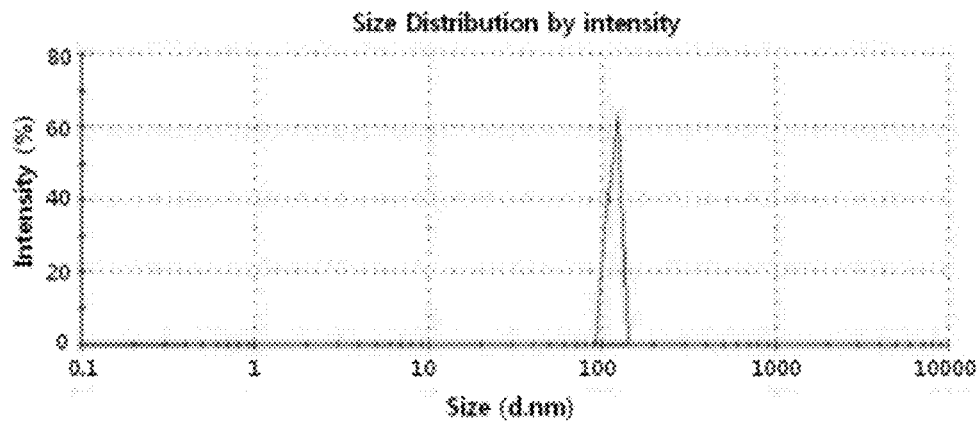
Figures 9C, 9D:
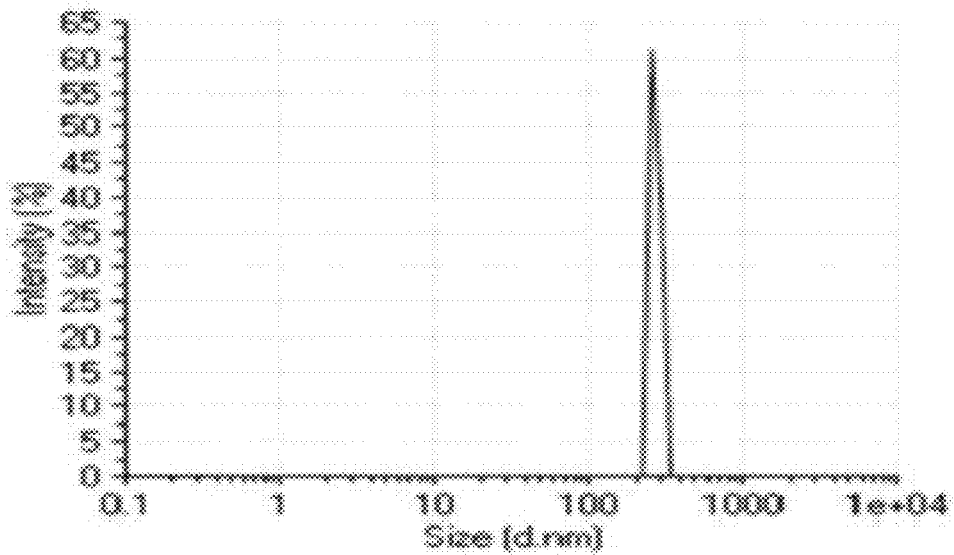

The loading efficiency (%) was obtained from the mole ratio of the actually encapsulated amount of the drug with respect to the added amount thereof for loading. As shown in FIG. 7, the loading efficiency of genistein, dexamethasone, doxorubicin, and epirubicin was found to be about 20% (FIG. 7a), about 2% (FIG. 7b), about 30% (FIG. 7c), and about 25% (no data was shown), respectively. Specifically, in case of genistein, the peak for the solvent was observed in about 2 minutes and about 3 minutes (in case of the purified drug, in about 3 minutes and about 6 minutes) and the peak for the drug was observed in about 21 minutes (in case of the purified drug, in about 20 minutes). In case of dexamethasone, the peak for the solvent was observed in 3 minutes (in the case of the purified drug, same results were obtained) and the peak for the drug as loaded was observed in about 16 minutes (in case of the purified drug, the peak was observed in a similar time).

As can be seen in the TEM images of FIG. 8, the hyaluronic acid-peptide micelles loaded with genistein (FIG. 8a), dexamethasone (FIG. 8b), doxorubicin (FIG. 8c), and epirubicin (FIG. 8d) had a spherical shape and were dispersed well. As shown in the expanded images (on the right side in FIGS. 8a to 8c) and FIG. 8d, the drug particles encapsulated inside the hyaluronic acid-peptide conjugate micelle were shown as dark black portions in the spherical micelles, and this confirmed that the drug particles were encapsulated in each micelle.

The diameter of each micelle particle was found to range from 100 to 300 nm, and these results were consistent with the results obtained by using the dynamic light scattering (DLS) apparatus. Specifically, the results of measuring DLS confirmed that as shown in FIGS. 9a to 9d, the monodispersed micelles with a size similar to what was shown in the TEM image and a narrow polydispersity index were formed.

EXPERIMENTAL EXAMPLE 5

Analysis of In Vitro Biological Activity of the Hyaluronic Acid-Peptide Conjugate 5-1) Analysis Method A $VEGF_{165}$ solution (with a concentration in PBS of 0.5 μg/mL) (R&D System) was put into 96-black well-plate, and reacted overnight at 4° C. to give a $VEGF_{165}$-coated well. After being washed with PBS, the well was blocked with a blocking buffer (which is a BSA solution with BSA(Sigma-Aldrich) dissolved therein at a concentration of 3 wt % in a PBS buffer solution at pH 7.4) and washed again with PBS (at room temperature for 2 hours). The solutions of the anti-Flt1 peptide (GGNQWFI) (SEQ ID NO: 3) comprising 20, 200, 2000, 20000 nM of the peptide (GGNQWFI) (SEQ ED NO: 3) and 500 ng/mL of Flt1-Fc (R&D systems, Minneapolis, Minn.) in a solution of BSA(Sigma-Aldrich) as dissolved in PBS (pH 7.4) at 1 wt %, or the solution of the hyaluronic acid-peptide conjugate with a lower peptide content of Preparation Example 3 test group (HA-GGNQWFI) (as prepared by conjugating 20 peptides per one HA-TBA molecule) was added to the $VEGF_{165}$-coated well, and incubated at room temperature for one hour. After that, the well was washed with PBS comprising 0.05 wt % of Tween 20 three times, and then a BSA (Sigma-Aldrich) solution (wherein BSA was dissolved in PBS at a concentration of 0.3 wt %) comprising anti-human IgG-HRP-Fc (Pierce, Rockford, Ill.) was placed therein and incubated at room temperature for one hour. Then, after the well was washed with a PBS comprising 0.05 wt % of Tween 20 three times and washed with a PBS once, the amount of the conjugated Flt1-Fc was measured with BM chemiluminescence ELISA substrate system (Victor 3 luminometer, PerkinElmer, Mass.). As a negative control group, the sample as not treated with Flt1-Fc was used, and as a positive control group, the sample treated with anti-Flt1 peptide but treated with Flt 1-Fc was used.

5-2) Analysis Results

The luminescence value of the positive control group without being treated with anti-FR1 peptide was set to be 100% and other data were normalized. The results are shown in FIG. 10.

Figure 10:
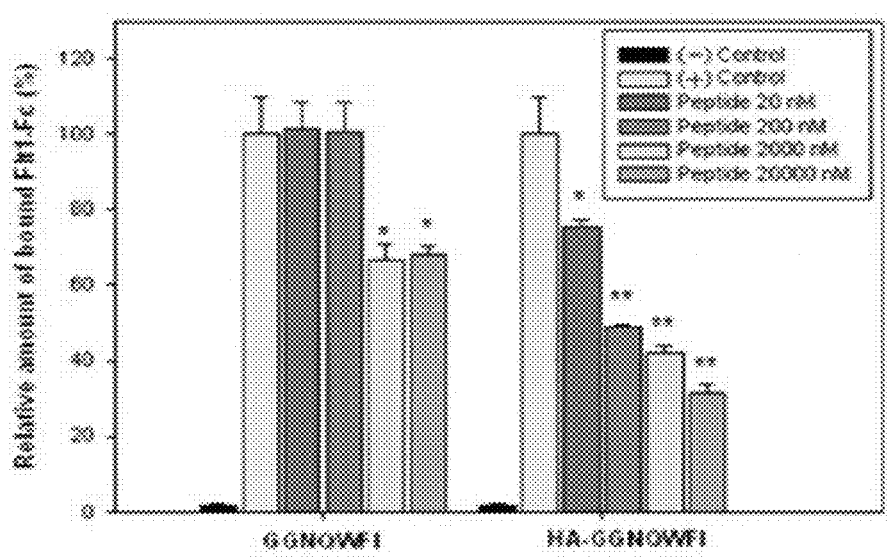
FIG. 10 is a view illustrating an effect of hyaluronic acid-peptide conjugate of Preparation Example 3 to inhibit the binding between Flt1-Fc and VEGF165 (with respect to the positive control group, * P<0.05 and ** P<0.01, n=3).

As shown in FIG. 10, the anti-FR1 peptide failed to inhibit the bonding between $VEGF_{165}$ and Flt1-Fc even at 200 mM. Further, even at a higher concentration of 2000 nM, 20000 nM, about 68% of $VEGF_{165}$ was bound to Flt1-Fc. In contrast, the hyaluronic acid-peptide conjugate inhibited the bonding between $VEGF_{165}$ and Flt1-Fc up to about 32% in a dose-dependent manner, indicating its in vitro biological activity. These results confirm that the hyaluronic acid-peptide conjugate has a superior effect of inhibiting the bonding between $VEGF_{165}$ and Flt1-Fc in comparison with the peptide not bound to hyaluronic acid.

EXPERIMENTAL EXAMPLE 6

Figure 11:
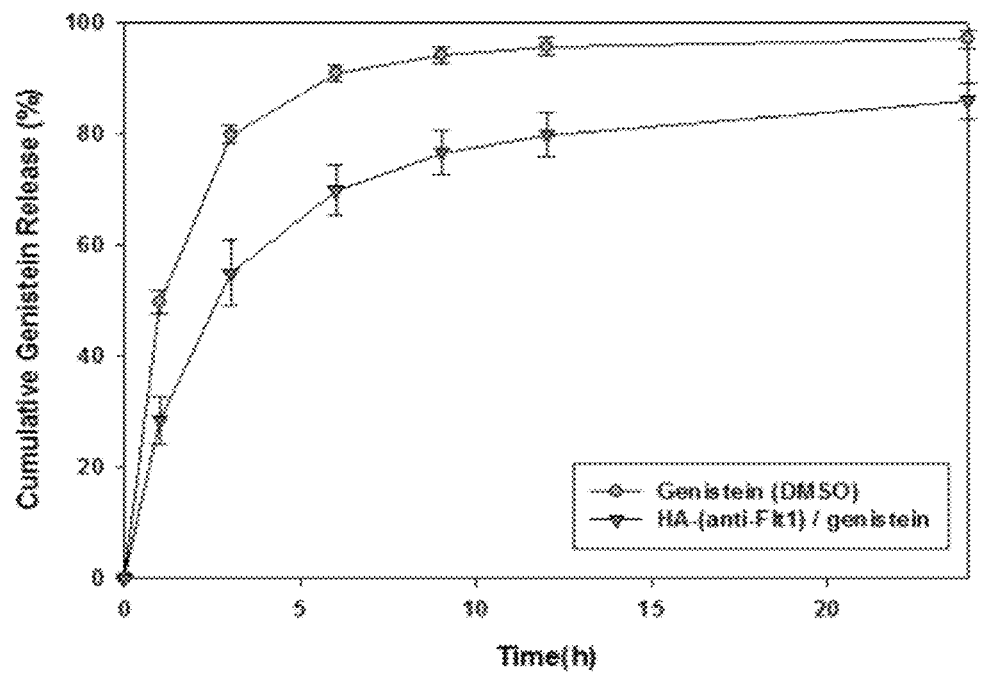
FIG. 11 is a view illustrating in vitro releasing tendencies of genistein in case of the genistein solution and in case of the genistein-loaded hyaluronic acid-peptide conjugate micelle (HA-(anti-Flt1)/genistein) in Example 1, respectively.

In Vitro Release Test of the Genistein-Loaded, Hyaluronic Acid-Peptide Conjugate Micelle 6-1) Analysis Method 2 mL of a solution of the genistein-loaded hyaluronic acid-peptide conjugate micelle of Example 1 and a solution comprising the same amount of genistein dissolved in 2 mL of DMSO were placed into a dialysis tube (MWCO: 10 KDa), respectively and immersed in 10 mL of a PBS solution (pH: 7.4) and then in vitro release tests were conducted at 37° C. The PBS solution comprising the released genistein was taken at a predetermined time and the concentration of genistein was measured by HPLC analysis to quantify the amount of the released genistein. The results are shown in FIG. 11. (see, Biomaterials 26 (2005) 5064-5074)

6-2) Analysis Results

As can be seen in FIG. 11, half of the amount of genistein encapsulated inside the hyaluronic acid-peptide micelle had been released for 3 hours, and then all the rest amount was released over 21 hours, indicating that genistein in the hyaluronic acid-peptide micelle was released more slowly than when it was not treated at all. As such, when genistein is loaded inside the hyaluronic acid-peptide conjugate micelle, it is slowly released from the micelle and thus it remains in a body for an extended period of time than when it is used alone, and accordingly one can obtain an enhanced remedial effect.

EXPERIMENTAL EXAMPLE 7

Analysis of In Vitro Anti-Angiogenic Effect of the Genistein-Loaded, Hyaluronic Acid-Peptide Conjugate Micelle 7-1) Analysis Method An endothelial cell, HUVEC (Human Umbilical Vein Endothelial Cell) (innopharmascreen co. ltd., Korea) was incubated in a EGM®² culture medium (Lonza) and then 100 µL of the cell solution with a concentration of $2 \times 10^4$/ml was distributed per each well and incubated in a 5% $CO_2$ cultivator at 37° C. for 16 hours. After 16 hours, the culture medium was replaced and seven types of samples were treated. Among the seven types of samples were the control group as treated only with a culture medium, and the groups treated with 50 µM, 100 µM, and 200 µM of genistein solutions and the solutions of the genistein-loaded hyaluronic acid-peptide conjugate of Example 1 comprising 50 µM, 100 µM, and 200 µM of genistein, respectively. 10 µL of each sample and 100 µL of the culture medium were mixed and treated. After the samples were treated, they were incubated in 5% $CO_2$ incubator at 37° C. and the culture media with the samples being mixed therein plowed once a day. After three days, the culture media were removed and the samples were treated with 110 µL of an MTT solution (Amresco Co. (Solon, Ohio)), and incubated in a cultivator at 37° C. for two hours and then 50 µL of DMSO was added thereto to measure a light absorbency at 540 nm. The light absorbance as measured was compared with the light absorbance of the control group and the degree of the cell growth was calculated.

7-2) Analysis Results

Figure 12:
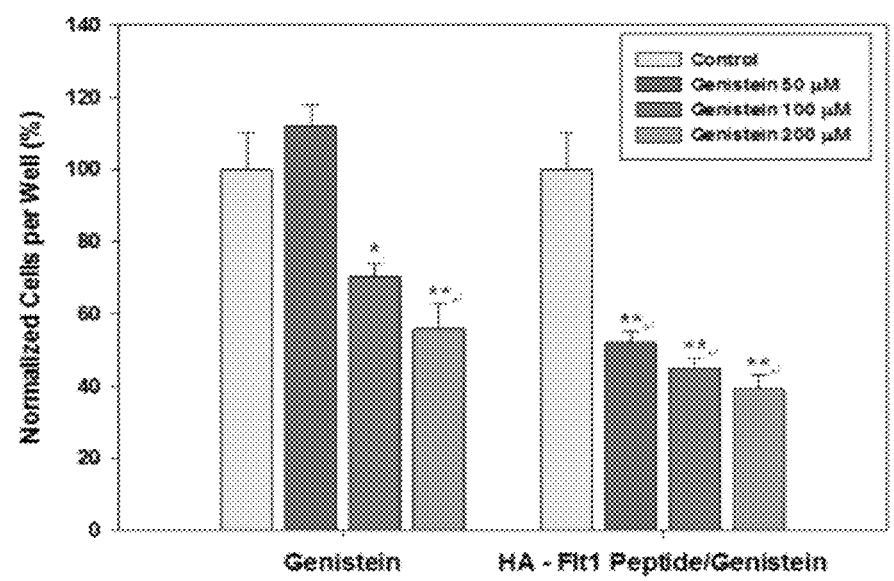
FIG. 12 is a view illustrating an effect of inhibiting the proliferation of HUVEC cell by the genistein-loaded, hyaluronic acid-peptide conjugate micelle (in comparison with the control group, *P<0.01 and **P<0.005, n=4).

As shown in FIG. 12, the genistein-loaded hyaluronic acid-peptide conjugate (HA-Flt1 Peptide/Genistein) of Example 1 showed an effect of inhibiting angiogenesis depending on the administered concentrations, which was superior to genistein alone, not encapsulated inside the micelle.

Specifically, when the cell number of the control group was set to be 100%, the group treated with genistein as not encapsulated inside the micelle showed a significant effect of inhibiting the cell growth (70.5±3.5%) at a concentration of 100 µm. At the same concentration, however, the cell number of the group treated with the genistein-loaded hyaluronic acid-peptide conjugate micelle was about 44.6±2.8%, decreasing by about 55.4% in comparison with the control group, and by about 26% in comparison with the group treated with genistein alone. It was also found that at a concentration of 200 uM, the group treated with genistein alone showed the best results, which were inferior to the results obtained from the group treated with the genistein-loaded micelle at its lowest concentration (50 uM).

Therefore, it can be confirmed that the genistein-loaded, hyaluronic acid-peptide conjugate micelle according to an embodiment of the present invention has an effect of inhibiting angiogenesis, which is significantly better than that of genistein alone as not encapsulated inside the micelle, not to mention the effect obtained from the control group.

EXPERIMENTAL EXAMPLE 8

Analysis of an Effect Inhibiting Corneal Neovascularization by the Hyaluronic Acid-Peptide Conjugate 8-1) Analysis Method In the experiment, 5 Albino Sprague Dawley male rats with an average body weight of 250 g were used per each group. All animal tests including this experiment were conducted in compliance with the guidelines of the Catholic University of Korea and the principles of laboratory animal care; NIH publication No. 85-23 revised in 1985.

The rat was put under anesthesia by an intra-peritoneal injection of a mixed solution of 20 mg/kg of ketamine hydrochloride and 2.5 mg/kg of xylazine hydrochloride. At the center of the right cornea, a silver nitrate applicator stick consisting of 75% (v/v) of silver nitrate and 25% (v/v) of potassium nitrate (diameter: 1 mm) was contacted with the cornea for 10 seconds to cauterize the same. In 3 days after the cauterization, subconjunctival administration was conducted with 20 µL of each of 4 sample solutions (a normal control group, NV control (neovascularization control: a control group wherein angiogenesis was made to occur and no drug was treated thereon), a solution comprising Avastin (Roche) dissolved in PBS at a concentration of 10 mg/ml, a solution comprising anti-Flt1 peptide (GGNQWFI) (SEQ ID NO: 3) dissolved in PBS at a concentration of 2.5 mg/ml, and a solution comprising the hyaluronic acid-peptide conjugate with a lower peptide concentration obtained from Preparation Example 3 as dissolved in PBS at a concentration of 2.5 mg/ml based on the content of anti-Flt1 peptide). The effect of inhibiting corneal neovascularization was observed with an ophthalmic microscope (Olympus, Tokyo, Japan). The obtained images were subjected to quantitative analysis with Image J program (Ver. 1.38, National Institute of Health, MD).

8-2) Analysis Results

As shown in FIG. 13, the most effective one in inhibiting the corneal neovascularization was the hyaluronic acid-peptide conjugate obtained from Preparation Example 3, followed by the anti-Flt1 peptide, and then Avastin.

The results of inhibiting corneal neovascularization by each of the sample solutions are shown in FIG. 14. As shown in FIG. 14, the average ratio of the neovascular area is 90.8±5% for the control group, 35.4±6.6% for Avastin (the positive control group), 27±5.7% for anti-Flt1 peptide, and 17.4±5.6% for the hyaluronic acid-peptide conjugate.

EXPERIMENTAL EXAMPLE 9

Analysis of an Effect of Inhibiting Retinal Choroidal Neovascularization by the Hyaluronic Acid-Peptide Conjugate 9-1) Analysis Method In the experiment, 6 Brovin-Norway (BN) male rats with an average body weight of 250 g were used per each group. Four groups consisted of a negative control group, a hyaluronic acid test group, an anti-Flt1 peptide (GGNQWFI) (SEQ ID NO: 3) test group, a test group of the hyaluronic acid-peptide conjugate with a higher peptide content as prepared from Preparation Example 3 (HA-GGNQWFI(2)). The anti-Flt1 peptide sample and the hyaluronic acid-peptide conjugate sample were made to have an identical peptide concentration of 10 mg/ml. First, the rat was put under anesthesia by being treated with 0.2 mL of a mixed solution (1:1) of 100 mg/ml of ketamine hydrochloride and 20 mg/ml of xylazine hydrochloride. After the pupil of the rat dilated by a local treatment with 0.8% (w/v) of tropicamide, choroidal neovascularization (CNV) was induced thereon with using a laser-photocoagulation at 532 nm (Visulas 532, Carl Zeiss, Germany) (spot size 100 µm, power 260 mA, exposure time 30 ms). In 3 days after the laser induced damage, 10 µL of each sample solution was injected into a vitreous body. The effect of inhibiting retinal and choroidal neovascularization was determined with a fluorescence microscope analysis using dextran-FITC (MW=40,000) after 2 weeks from the laser-induced damage. After being put under anesthesia, the rat was injected with 500 μL of a dextran-FITC solution (25 mg/mL) at its tail vein, and in 5 minutes, the choroid was separated and observed with a fluorescence microscope equipped with a digital camera (Olympus, Tokyo, Japan). The obtained images were analyzed with Image J program (NIH, Bethesda, Md.).

9-2) Analysis Results

As can be seen in FIG. 15a, a high intensity of fluorescence and a large damage of the Bruch's membrane were observed in the negative control group and the hyaluronic acid test group, while a low intensity of fluorescence and a small damage were observed in the anti-Flt1 peptide (GGNQWFI) (SEQ ID NO: 3) test group and the test group of the hyaluronic acid-peptide conjugate. Moreover, in the test group of the hyaluronic acid-peptide conjugate, the retinal and choroidal neovascularization was more effectively inhibited than in the anti-Flt1 peptide test group.

For the results as shown in FIG. 15a, the fluorescence intensity of the negative control group was set to be 100% and then the relative intensity of the fluorescence in the other test groups was compared therewith and quantitatively analyzed. The results are shown in FIG. 15b. The average intensity of the fluorescence (%) was 97.1±4.7% for the hyaluronic acid test group, 61.4±4.4% for the anti-Flt 1 peptide test group, and 48.9±3.9% for the test group of the hyaluronic acid-peptide conjugate. Statistical analysis through t-test confirms that the fluorescence intensities of the anti-Flt1 peptide test group and the test group of the hyaluronic acid-peptide conjugate were significantly decreased in comparison with that of the negative control group and the hyaluronic acid test group (**$P<0.01$), and that the effect of inhibiting the retinal and choroidal neovascularization by the hyaluronic acid-peptide conjugate was better than that of the anti-FR1 peptide ($P=0.0004$)

EXPERIMENTAL EXAMPLE 10

Analysis of an Effect Inhibiting Vascular Hyperpermeability Due to Diabetic Retinopathy by the Hyaluronic Acid-Peptide Conjugate 10-1) Analysis Method In the experiment, 10 Sprague Dawley (SD) male rats with an average body weight of 250 g were used per one group. Four groups consisted of a hyaluronic acid test group, an anti-Flt1 peptide (GGNQWFI) (SEQ ID NO: 3) test group, a test group of the hyaluronic acid-peptide conjugate with a lower peptide content (with 20 peptides being conjugated per one molecule of HA-TBA) as prepared from Preparation Example 3 (HA-GGNQWFI), and a test group of the hyaluronic acid-peptide conjugate with a higher peptide content (with 28 peptides being conjugated per one molecule of HA-TBA) as prepared from Preparation Example 3(HA-GGNQWFI(2)). The anti-Flt1 peptide sample and the hyaluronic acid-peptide conjugate samples were made to have an identical peptide concentration of 5 mg/ml. First, each rat was injected intraperitoneally with 60 mg/kg of streptozotocin dissolved in 10 mM citrate buffer at pH 4.5 in order for diabetes to be induced. In three days after the injection of streptozotocin, the rat was determined to develop diabetes when its serum concentration of glucose was at least 300 mg/dL. In a week after the injection of streptozotocin, 10 μL of each sample solution was injected into the vitroeus body. In four weeks after the injection of streptozotocin, the effect of inhibiting vascular hyperpermeability due to diabetic retinopathy was determined by the fluorescence microscopic analysis with using dextran-FITC (MW=10,000) in the same manner as set forth in Experimental Example 7-1.

In addition, changes in the structure of the retinal blood vessel were observed with an electron microscope. The retina as taken out from the rat was fixed with 4 wt % of glutaraldehyde and 1 wt % of osmium tetroxide, dehydrated with ethanol, and then embedded in an Epon mixture. After that, the sample was cut and observed with a transmission electron microscope (JEM-1010, JEOL, Tokyo, Japan).

10-2) Analysis Results

As shown in FIG. 16a, in case of the hyaluronic acid test group, the vascular hyperpermeability due to diabetic retinopathy cause the fluorescence of the dextran-FITC to be diffused into the retinal parenchyma. In the anti-Flt1 peptide test group and the test groups of the hyaluronic acid-peptide conjugates (HA-GGNQWFI, HA-GGNQWFI(2)), virtually no fluorescence of the dextran-FITC was observed throughout the retinal parenchyma and most of the fluorescence was observed in the blood vessel. In the test groups of the hyaluronic acid-peptide conjugates (HA-GGNQWFI, HA-GGNQWFI(2)), the vascular hyperpermeability due to diabetic retinopathy was inhibited more effectively than in the anti-Flt1 peptide test group wherein no peptide was conjugated to hyaluronic acid.

For the results as shown in FIG. 16a, the fluorescence intensity of the hyaluronic acid test group was set to be 100% and then the relative intensity of the fluorescence in the other test groups was compared therewith and quantitatively analyzed. The results are shown in FIG. 16b. The average intensity of the fluorescence (%) was 79.0±9.2% for the anti-Flt1 peptide test group, 58.4±7.8% for the test group of the hyaluronic acid-peptide conjugate with a lower peptide content (HA-GGNQWFI), and 51.3±10.8% for the test group of the hyaluronic acid-peptide conjugate with a higher peptide content (HA-GGNQWFI(2)) (see, FIG. 16b). Statistical analysis through t-test showed that in comparison with the hyaluronic acid test group, the fluorescence intensities of the anti-Flt1 peptide test group and the test groups of the hyaluronic acid-peptide conjugates were significantly decreased ($P<0.01$), and the inhibiting effect of the hyaluronic acid-peptide conjugate was better than that of the anti-Flt1 peptide ($P<0.01$). Moreover, the inhibiting effect of the hyaluronic acid-peptide conjugate with a higher peptide content was better than that of the hyaluronic acid-peptide conjugate with a lower peptide content ($P=0.1$).

As can be seen in FIG. 17, in the negative control group of diabetic retinopathy, the vascular basement membrane had an irregular and corrugated shape surrounded by a thin layer of endothelial cells. However, in the anti-Flt1 peptide test group, the blood vessel had a rounded shape although the endothelial cell layer was thin. In the test group of the hyaluronic acid-peptide conjugate with a higher peptide content (HA-GGNQWFI(2)) of Preparation Example 3, the endothelial cell layer was as thick as in the normal control group and the blood vessel had a round shape, as well.

EXPERIMENTAL EXAMPLE 11

Analysis of Pharmacokinetic (PK) Characteristics in the Eyeball of the Hyaluronic Acid-Peptide Conjugate 11-1) Analysis Method In the experiment, 6 Sprague Dawley (SD) male rats with an average body weight of 250 g were used per one group.

Three groups consisted of a hyaluronic acid (HA) test group, an anti-Flt1 peptide (GGNQWFI) (SEQ ID NO: 3) test group, and a test group of the hyaluronic acid-peptide conjugate with a lower peptide content as prepared from Preparation Example 3 (HA-GGNQWFI). The anti-Flt1 peptide sample and the hyaluronic acid-peptide conjugate sample were made to have an identical peptide concentration of 5 mg/ml. 10 μL of each sample solution was injected into the vitroeus body, which was sampled in 6 hours, 1 day, 3 days, 7 days, 10 days, and 14 days and stored at −20° C. until analysis. The concentration of the anti-Flt1 peptide in the vitreous body was measured with fluorescence analysis. Specifically, the vitreous body was disintegrated by using 200 μL of RIPA buffer, and then subjected to centrifugation under 14,000 g at 4° C. for 10 minutes to provide a supernatant solution. By using a spectrofluorometer (Cary Eclipse Fluorescence Spectrophotometer, Varian, Australia), the photoluminescence of each sample was measured at an excitation wave length of 280 nm and an emission wavelength of 350 nm. The vitreous body of the SD rat that was not treated at all was used as a blank control.

11-2) Analysis Results

As shown in FIG. 18a, the concentration of the vitreous body from the anti-Flt1 peptide (GGNQWFI) (SEQ ID NO: 3) test group was reduced to the base line before 10 days elapsed and its Tmax was 24 hours, but the concentration of the hyaluronic acid-conjugate was maintained for at least 14 days and Tmax was 6 hours. The reason why the anti-Flt1 peptide has a longer Tmax seems that the anti-Flt1 peptide is water-insoluble. The Cmax of the hyaluronic acid-peptide conjugate was 1.6±0.6 mg/mL, higher than that of anti-Flt1 peptide (0.8±0.7 mg/mL). Despite being at the same dose, the hyaluronic acid-peptide conjugate has a higher AUC than that of the anti-Flt1 peptide, indicating that the bioavailability (AUC/dose) of the anti-Flt1 peptide was enhanced after the conjugation to hyaluronic acid.

EXPERIMENTAL EXAMPLE 12

Analysis of the Effect Treating Asthma by the Hyaluronic Acid-Peptide Conjugate 12-1) Analysis Method The biological activity of the hyaluronic acid-peptide conjugate with a lower peptide concentration (HA-GGNQWFI) in accordance with Preparation Example 3 was measured through the reaction to methacholine. Specifically, as to the airway hyper-responsiveness (AHR), the laboratory rat (in vivo) was made to keep exercising naturally without being put under anesthesia and the enhanced pause (Penh), the number reflecting the airway obstruction as represented by Mathematical Equation 1 was measured by using plethysmography. In this experimentation was used a non-invasive method wherein the measurement was conducted without correcting or putting the laboratory animal under anesthesia.

$$Penh=[(Te/RT-1)\times(PEF/PIF)] \quad \text{[Mathematical Equation 1]}$$

In Mathematical Equation 1, Te represents an expiratory time (seconds), RT represents a relaxation time (seconds), PEF represents a peak expiratory flow (ml), and PIF represents a peak inspiratory flow (ml/s).

As the laboratory mouse, BALB/c mice (female, 6 week old, 5 per each group) were used. Five groups consisted of a normal control group (PBS-PBS: wherein asthma was not induced and the mice were treated with PBS), a negative control group (OVA/LPS10-OVA: wherein asthma was induced by using OVA and LPS, and the mice were treated with PBS only), a hyaluronic acid test group, an anti-Flt1 peptide (GGNQWFI) (SEQ ID NO: 3) test group, and a test group of the hyaluronic acid-peptide conjugate obtained from Preparation Example 3. The dose of the hyaluronic acid-peptide conjugate was changed between 10 mg/head and 1,000 mg/head.

First, in order to make a mouse asthma model, each mouse was sensitized by intranasal administration of 75 μg of ovalbumin (OVA) (Calbiochem, La Jolla, Calif.) and 10 μg of lipopolysaccharide (LPS) (Calbiochem, La Jolla, Calif.) on 0 day, the first day, the second day, and the 7th day. Then, OVA (50 ug/head), hyaluronic acid (500 μg/head), anti-Flt1 peptide (GGNQWFI) (SEQ ID NO: 3) (10, 30, 100, 300, 1000 μg/head), and the hyaluronic acid-peptide conjugate with a low peptide content prepared from Preparation Example 3 (10, 30, 100, 300, 1000 mg/head, based on the peptide content) were intranasally administered, respectively, after 14 days, 15 days, 21 days, 22 days to challenge. The mice in the negative control group were administered with OVA alone over the entire period and the mice in the normal control group were injected with PBS alone on the 14th day, the 15th day, the 21th day, and the 22th day. The evaluation on the methacholine airway hyper-responsiveness and a lung inflammation was made in 24 hours and 48 hours after the last allergen challenge, respectively.

The pulmonary function was measured on the 23th day by using the non-invasive whole body plethysmographs for the mouse that was not put under anesthesia. The laboratory mouse was placed onto the plethysmography chamber and exposed to the PBS aerosol (a basic measurement) and the metahcholine aerosol at a concentration of 6.25, 12.25, 25, and 50 mg/mL. The aerosol was prepared by using an ultrasonic nebulizer and the laboratory mouse was exposed to methacholine for 3 minutes and then the Penh was measured for 5 minutes.

12-2) Analysis Results

As can be seen in FIG. 19, in 24 hours after the last challenge of allergen, the methacholine airway hyper-responsiveness of the hyaluronic acid-peptide conjugate treated group was greatly reduced to a level similar to that of the normal control group wherein no asthma was induced. The hyaluronic acid and the anti-Flt1 peptide that was not conjugated to hyaluronic acid had an effect of reducing the methacholine airway hyper-responsiveness, which was inferior to the hyaluronic acid-peptide conjugate.

As can be seen in FIG. 20, in the hyaluronic acid-peptide conjugate treated group, bronchoalveolar lavage (BAL) cellularity, the index for the lung inflammation, sharply decreased and was found to be dose-dependent. In particular, in the hyaluronic acid-peptide conjugate treated group at a concentration of 1000 μg/head, the bronchoalveolar lavage cellularity was less than half of the cellularity in the negative control group.

EXPERIMENTAL EXAMPLE 13

Analysis of an Effect Inhibiting Corneal Neovascularization by the Genistein-Loaded Hyaluronic Acid-Peptide Conjugate 13-1) Analysis Method In the experimentation, 5 Albino Sprague Dawley male rats with an average body weight of 250 g were used per each group.

The effect of inhibiting corneal neovascularization was analyzed in the same manner as set forth in Experimental Example 8, except for using a normal control group, a negative control group (NV control: neovascularization control wherein angiogenesis was induced and then no drug was treated thereto), a solution comprising Avastin (Roche) as dissolved in PBS at a concentration of 10 mg/ml, a solution of the hyaluronic acid-peptide conjugate with a lower peptide content (HA-GGNQWFI) of Preparation Example 3 as dissolved in PBS at a concentration of 3.2 mg/ml based on the peptide content, the dispersions of genistein as dispersed in two different solvents (i.e., PBS, DMSO) in an amount of 6.2 mg/ml, respectively, a sample solution of the genistein-loaded hyaluronic acid-peptide conjugate micelle obtained according to Example 1 as dissolved in PBS at a concentration of 3.2 mg/ml based on the peptide content.

13-2) Analysis Results

As can be seen in FIG. 21, the test group of the genistein-loaded hyaluronic acid-peptide conjugate micelle as obtained according to Example 1 had an inhibiting effect superior to the genistein test group (two solvent test group), the hyaluronic acid-peptide conjugate test group, the Avastin test group, indicating that it inhibited the corneal neovascularization most effectively.

The results of inhibiting corneal neovascularization obtained from each sample were quantitatively analyzed, and the results are shown in FIG. 22. Specifically, the average ratio of the neovascular area was 86% for the control group, 23% for the positive control group treated with Avastin, 30% for the hyaluronic acid-peptide conjugate test group, 68% for the group treated with genistein as dispersed in water, 38% for the group treated with genistein as dissolved in DMSO, and 20% for the test group of the genistein-loaded, hyaluronic acid-peptide conjugate.

EXPERIMENTAL EXAMPLE 14

Analysis of an Effect Inhibiting Vascular Hyperpermeability Due to Diabetic Retinopathy by the Genistein-Loaded Hyaluronic Acid-Peptide Conjugate Micelle 14-1) Analysis Method In the experiment, 5 Sprague Dawley (SD) male rats with an average body weight of 250 g were used per each group. A normal control group, a negative control group (wherein diabetes was induced but there was no sample treatment), a solution of Avastin as dissolved in PBS at a concentration of 10 mg/ml, a test group of the hyaluronic acid-peptide conjugate with a lower peptide content (20 peptides being conjugated per one molecule of HA-TBA) of Preparation Example 3 (HA-(anti-Flt1 (GGNQWFI))), genistein as dispersed in two different solvents (DIW, DMSO) in an amount of 6.2 mg/ml, respectively, a sample solution of the genistein-loaded hyaluronic acid-peptide conjugate micelle according to Example 1 (HA-(anti-Flt1)/genistein) as dissolved in PBS at a concentration of 3.2 mg/ml based on the peptide content were used. In the same manner as set forth in Experimental Example 10, diabetes was induced and the groups were treated with the sample solutions. The effect inhibiting vascular hyperpermeability due to diabetic retinopathy was determined with a fluorescent microscopic analysis by using dextran-FITC (MW=10,000) in four weeks after administration of streptozotocin (in the same manner as set forth in Experimental Example 10.

14-2) Analysis Results

As can be seen in FIG. 23a, in the test group of the genistein-loaded hyaluronic acid-peptide conjugate micelle, virtually no fluorescence of the dextran-FITC was observed in retinal parenchyma, and the majority of the fluorescence was found in the blood vessel. Such an effect inhibiting vascular hyperpermeability by the genistein-loaded hyaluronic acid-peptide micelle was better than those of the hyaluronic acid-peptide conjugate with no genistein encapsulated therein, genistein as untreated, and Avastin as used in the positive control group.

Based on the results as shown in FIG. 23a, the fluorescence intensity of the normal test group was set to be one (1) and then the relative intensity of the fluorescence in each of other test groups was compared therewith and quantitatively analyzed. The results are shown in FIG. 23b. The average intensity of the fluorescence in the negative control group sharply increased to 2.54±0.20, and the intensity in the test group of the genistein-loaded hyaluronic acid-peptide conjugate micelle in accordance with an embodiment of the present invention was reduced the most to 1.23±0.20. Besides, the average intensity of the fluorescence was 1.49±0.17 for the Avastin test group, 1.58±0.17 for the hyaluronic acid-peptide conjugate (HA-(anti-Flt-1)) test group, 2.00±0.16 for genistein as dissolved in DMSO, and 2.38±0.20 for genistein as dispersed in water. (see, FIG. 23b) Statistical analysis through t-test revealed that the test group of the genistein-loaded hyaluronic acid-peptide conjugate micelle had a significantly decreased fluorescence intensity in comparison with the genistein (DMSO) control group (*P=0.02), and was observed to have an inhibiting effect still better than the hyaluronic acid-peptide conjugate group (**P=0.0002).

EXPERIMENTAL EXAMPLE 15

Evaluation of Capability Targeting Tumor by the Doxorubicin-Loaded Hyaluronic Acid-Peptide Conjugate Micelle 15-1) Analysis Method Balb/c nude mice (4 week old, 25 g, male, one for each group) were used as the laboratory mouse. First, mouse melanoma B16F10 cells ($1 \times 10^6$ cells) (Korean Cell line bank) were subcutaneously injected on the right back of the mouse to generate a tumor. After 14 days, the doxorubicin-loaded hyaluronic acid-peptide conjugate micelle obtained according to Example 3 was administered thereto via an intravenous injection at a concentration of 100 μg/head. In 6 hours after the injection, the fluorescence intensity of the micelle distributed in each tissue was measured through a fluorescent imaging (ref., ACS Nano, 4, 3005-3014 (2010)).

15-2) Analysis Results

As can be seen in FIG. 24, it was found that the doxorubicin-loaded hyaluronic acid-peptide conjugate micelle was accumulated in the liver, the kidney, the bladder, tumor. Such results confirmed that it can be developed as a drug delivery system targeting the liver tissue and liver tumor. In other words, it was accumulated in the tissue by receptor mediated endocytosis of the hyaluronic acid derivatives present in the liver and tumor and the results as shown in FIG. 24 can be obtained (Ref.: PCT/KR2010/006270, ACS Nano, 4, 3005-3014 (2010)).

EXPERIMENTAL EXAMPLE 16

Analysis of an Anticancer Effect Against Liver Cancer by the Epirubicin-Loaded, Hyaluronic Acid-Peptide Conjugate 16-1) Analysis Method The experiment was carried out by using 5 Sprague Dawley (SD) male rats with an average body weight of 250 g per each group. With the test groups treated with PBS, the hyaluronic acid-peptide conjugate with a lower peptide conjugate (HA-GGNQWFI) of Preparation Example 3, epirubicin, and the epirubicin-loaded hyaluronic acid peptide conjugate micelle (HA-micell) of Example 4, respectively, the experimentations were carried out.

First, 50 mg/kg of diethylnitrosamine (DEN) was intraperitoneally injected into each rat to induce a liver cancer model for 10 weeks. Then, to the liver cancer model thus prepared was administered a solution of each sample as dissolved in PBS once every five days in a total of 3 times via intravenous injection. The dose of each sample was set to be such an amount that 2 mg/head of epirubicin was administered and the dose of the epirubicin-loaded hyaluronic acid-peptide conjugate micelle as determined according to this standard was dissolved in PBS at a concentration of 2 mg/ml based on the conjugate and administered to the model. In 20 days after administration, the level of proliferating cell nuclear antigen (PCNA) in the liver tissue was determined through the western blot by measuring the thickness of each band.

16-2) Analysis Results

As can be seen in FIG. 25, the PCNA level of the epirubicin-loaded hyaluronic acid-peptide conjugate micelle was found to be much higher than that of the other groups. The PCNA results indicate that a drug has an effect restoring the DNA damaged by the growth of cancer cells. Therefore, it can be confirmed that the epirubicin-loaded hyaluronic acid-peptide conjugate micelle showing exceptionally high level of the PCNA has an anti-cancer effect superior to other groups.

What is claimed is:

1. A drug delivery composition, comprising:
a micelle consisting of a shell region comprising hyaluronic acid (HA) or its pharmaceutically acceptable salt, and a core region comprising a water-insoluble peptide with a terminal amine group, wherein the water-insoluble peptide is bound to said hyaluronic acid or its pharmaceutically acceptable salt; and
a water-insoluble drug loaded inside the micelle,
wherein the hyaluronic acid is a compound HA-tetra-n-butyl ammonium hydroxide complex as represented by Chemical Formula 1:

[Chemical Formula 1]

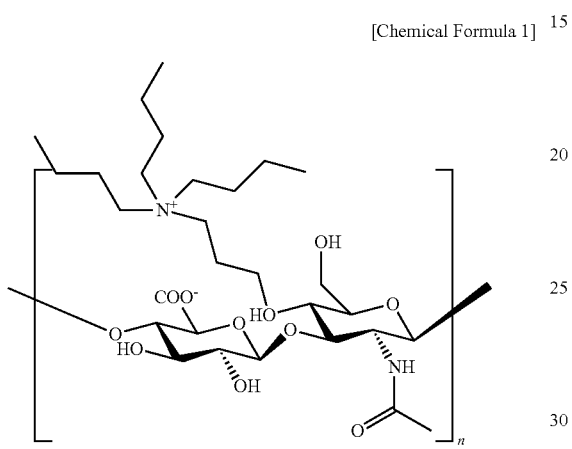

wherein n is an integer of 50 to 10,000, and the water-insoluble peptide is an antagonist peptide against VEGFR1 (anti-Flt1).

2. The drug delivery composition according to claim 1, wherein the water-insoluble peptide is bound with the number of its molecules corresponding to an integer of 4 to 15% of the number of the units per one molecule of the compound of Chemical Formula 1.

3. The drug delivery composition according to claim 1, wherein the water-insoluble peptide is either a peptide comprising lysine or glycine at the N-terminal, or a peptide having lysine or glycine additionally introduced at the N-terminal or the C-terminal.

4. The drug delivery composition according to claim 1, wherein the water insoluble peptide is at least one selected from the group consisting of GNQWFI(SEQ ID NO: 1), KGNQWFI(SEQ ID NO: 2), and GGNQWFI(SEQ ID NO: 3).

5. The drug delivery composition according to claim 1, wherein the water-insoluble drug is an angiogenesis inhibitor, an inhibitor of vascular hyperpermeability due to diabetic retinopathy, an asthma drug, or an anti-cancer drug.

6. The drug delivery composition according to claim 5, wherein the water-insoluble drug is at least one selected from the group consisting of genistein, dexamethasone, doxorubicin, and epirubicin.

7. The drug delivery composition according to claim 1, wherein the micelle is loaded with the water-insoluble drug in an amount of 0.1 to 70% by weight with respect to the total weight of the micelle.

8. The drug delivery composition according to claim 1, wherein the water-insoluble drug loaded micelle has a diameter of 100 to 300 nm.

9. A method of producing a drug-loaded, hyaluronic acid-peptide conjugate micelle, which comprises the steps of:

reacting hyaluronic acid (HA) or its pharmaceutically acceptable salt with tetra-n-butyl ammonium hydroxide (TBA-OH) to prepare HA-TBA of Chemical Formula 1;
preparing a water-insoluble peptide with a terminal amine group;
reacting a carboxylic group of the prepared HA-TBA with the terminal amine group of the water-insoluble peptide in the presence of an organic solvent to prepare a hyaluronic acid-peptide conjugate micelle; and
loading a water-insoluble drug into the prepared micelle:

[Chemical Formula 1]

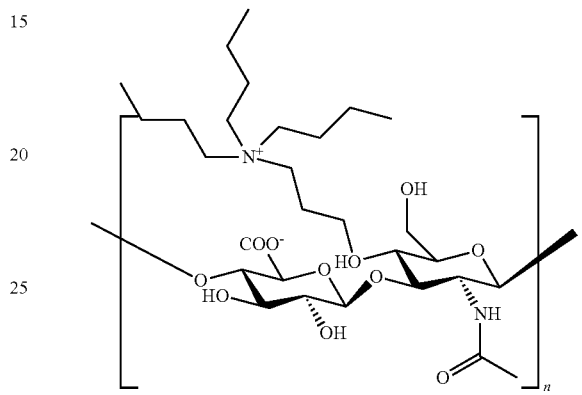

wherein n is an integer of 50 to 10,000, and the water-insoluble peptide is anti-Flt1 peptide that is an antagonist peptide against VEGFR1.

10. The production method according to claim 9, wherein the preparation step of the HA-TBA comprises the steps of:
reacting an ion exchange resin with tetra-n-butyl ammonium hydroxide (TBA-OH); and
further adding and reacting hyaluronic acid (HA) or its pharmaceutically acceptable salt.

11. The production method according to claim 9, wherein the water-insoluble peptide with the terminal amine group is a peptide prepared by further introducing lysine or glycine to the N-terminal or the C-terminal.

12. The production method according to claim 9, wherein the organic solvent is at least one selected from the group consisting of dimethyl sulfoxide (DMSO), dimethylformamide (DMF), dimethylacetamide, N-methyl-2-pyrrolidone (NMP), and hexamethylphosphoramide (HMPA).

13. The production method according to claim 9, wherein prior to carrying out the preparation step of the micelle, it further comprises the step of activating the HA-TBA by adding it to at least one activator selected from the group consisting of Benzotriazole-1-yl-oxy-tris(dimethylamino) phosphonium hexafluorophosphate (BOP), 1,3-Dicyclohexylcarbodiimide (DCC) and 1,3-Diisopropylcarbodiimide (DIC).

14. The production method according to claim 9, wherein the preparation step of the micelle comprises further adding N,N-diisopropyl ethylamine (DIPEA), 2,2,6,6-tetramethylpiperidine, or a mixture thereof to react the carboxylic group of the HA-TBA with the terminal amine group of the water-insoluble peptide.

15. The production method according to claim 9, wherein the hyaluronic acid or its pharmaceutically acceptable salt has a molecular weight of 10,000 to 3,000,000 Dalton (Da).

16. The production method according to claim 9, wherein the preparation step of the micelle comprises reacting the water-insoluble peptide with the number of its molecules corresponding to an integer of 5 to 20% of the numbers of the units per one molecule of the HA-TBA.

17. The production method according to claim 9, wherein the water-insoluble peptide is at least one selected from the group consisting of GNQWFI(SEQ ID NO: 1), KGNQWFI (SEQ ID NO: 2), and GGNQWFI(SEQ ID NO: 3).

18. The production method according to claim 9, wherein the step of loading the water-insoluble drug into the micelle comprises the steps of
dissolving the prepared micelle in an aqueous solvent to prepare a micelle solution;
dissolving the water-insoluble drug in an organic solvent to prepare a water-insoluble drug solution; and
mixing the micelle solution and the water-insoluble drug solution.

19. The production method according to claim 18, wherein the organic solvent is at least one selected from the group consisting of dimethyl sulfoxide (DMSO), dimethylformamide (DMF), dimethylacetamide, N-methyl-2-pyrrolidone (NMP), hexamethylphosphoramide (HMPA), ethanol, and chloroform.

20. The production method according to claim 18, wherein the preparation step of the micelle solution comprises dissolving the micelle in an aqueous solvent at a concentration of 0.5 mg/ml to 5 mg/ml.

21. The production method according to claim 18, wherein the step of preparing the water-insoluble drug solution comprises dissolving the water-insoluble drug in an organic solvent at a concentration of 0.5 mg/ml to 15 mg/ml.

22. The production method according to claim 9, wherein the micelle is loaded with the water-insoluble drug in an amount of 0.1 to 70% by weight with respect to the total weight of the micelle.

23. The production method according to claim 9, wherein the water-insoluble drug is at least one selected from the group consisting of genistein, dexamethasone, doxorubicin, and epirubicin.

24. A drug delivery composition, comprising:
a micelle consisting of a shell region comprising hyaluronic acid (HA) or its pharmaceutically acceptable salt, and a core region comprising a water-insoluble peptide with a terminal amine group, wherein the water-insoluble peptide is bound to said hyaluronic acid or its pharmaceutically acceptable salt; and
a water-insoluble drug loaded inside the micelle,
wherein the water-insoluble peptide is an antagonist peptide against VEGFR1 (anti-Flt1).

* * * * *